United States Patent
Cockerill et al.

(10) Patent No.: US 6,207,669 B1
(45) Date of Patent: *Mar. 27, 2001

(54) BICYCLIC HETEROAROMATIC COMPOUNDS AS PROTEIN TYROSINE KINASE INHIBITORS

(75) Inventors: George Stuart Cockerill, Bedford; Malcolm Clive Carter, Ware; Stephen Barry Guntrip, Hertford; Kathryn Jane Smith, Bishop's Stortford, all of (GB)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/214,261

(22) PCT Filed: Jul. 11, 1997

(86) PCT No.: PCT/EP97/03673

§ 371 Date: Dec. 31, 1998

§ 102(e) Date: Dec. 31, 1998

(87) PCT Pub. No.: WO98/02437

PCT Pub. Date: Jan. 22, 1998

(30) Foreign Application Priority Data

Jul. 13, 1996 (GB) .................................................... 9614756
Dec. 7, 1996 (GB) .................................................... 9625495

(51) Int. Cl.⁷ ...................... C07D 487/04; A61K 31/505
(52) U.S. Cl. ............................................. 514/258; 544/279
(58) Field of Search .............................. 514/258; 544/279

(56) References Cited

U.S. PATENT DOCUMENTS

| 4,166,735 | 9/1979 | Pilgrim .................................. | 71/118 |
| 5,654,307 | 8/1997 | Bridges et al. ....................... | 514/258 |

FOREIGN PATENT DOCUMENTS

| 2 254 549 | 7/1975 | (FR) . |
| WO 95 19774 | 7/1995 | (WO) . |
| WO 97 13771 | 4/1997 | (WO) . |

OTHER PUBLICATIONS

G. W. Rewcastle et al: "Tyrosine Kinase Inhibitors. 10. Isomeric 4–[(3–bromophenyl)amino]pyrido[d]pyrimidines are potent ATP binding sit inhibitors of the tyrosine kinase function of the epidermal growth factor receptor" Journal of Medicinal Chemistry, vol. 39, No. 9, 1996, Washington, U.S., pp. 1823–1835.

Y. Katsura et al: "Studies on antiulcer drugs. V. Synthesis and antiulcer activity of aralkylbenzozoles", Chemical and Pharmaceutical Bulletin, vol. 40, No. 8, 1992, Tokyo, JP, pp. 2062–2072.

T. Shoda et al: "Studies on antidiabetic agents. II. Synthesis of 5–[4–(methylcyclohexylmethoxy)benzyl]thiazolidine–2, 4–dione and its derivatives", Chemical and Pharmaceutical Bulletin, vol. 30, 1982, Tokyo, JP, pp. 3580–3600.

G. W. Rewcastle et al: "Synthesis of 6–substituted pyrido [3,d–d]pyrimidine–4(3H)–ones via directed lithiation of 2–substituted 5–aminopyridine derivatives", Journal of the Chemical Society, Perkin Transactions 1., 1996, Letchworth, GB, pp. 2221–2226.

*Primary Examiner*—Mukund J. Shah
*Assistant Examiner*—Deepak R. Rao
(74) *Attorney, Agent, or Firm*—John L. Lemanowicz

(57) ABSTRACT

Substituted heteroaromatic compounds, and in particular substituted bicyclic heteroaromatic compounds in which one ring is a pyridine or pyrimidine of formula (I) are protein tyrosine kinase inhibitors. The compounds are described as are methods for their preparation, pharmaceutical compositions including such compounds and their use in medicine, for example in the treatment of cancer and psoriasis.

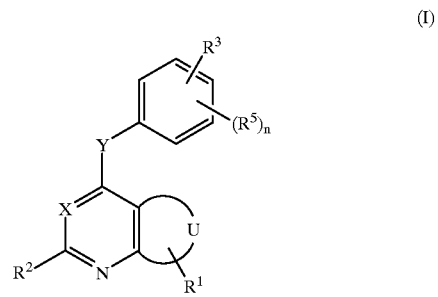

29 Claims, No Drawings

BICYCLIC HETEROAROMATIC COMPOUNDS AS PROTEIN TYROSINE KINASE INHIBITORS

This application is a 371 of PCT/EP97/03673 filed Jul. 11, 1997.

The present invention relates to a series of substituted heteroaromatic compounds, methods for their preparation, pharmaceutical compositions containing them and their use in medicine. In particular, the invention relates to bioisosteres of quinoline and quinazoline derivatives which exhibit protein tyrosine kinase inhibition.

Protein tyrosine kinases catalyse the phosphorylation of specific tyrosyl residues in various proteins involved in the regulation of cell growth and differentiation (A. F. Wilks, Progress in Growth Factor Research, 1990, 2, 97–111; S. A. Courtneidge, Dev. Supp.l, 1993, 57–64; J. A. Cooper, Semin. Cell Biol., 1994, 5(6), 377–387; R. F. Paulson, Semin. Immunol., 1995, 7(4), 267–277; A. C. Chan, Curr. Opin. Immunol., 1996, 8(3), 394–401). Protein tyrosine kinases can be broadly classified as receptor (e.g. EGFr, c-erbB-2, c-met, tie-2, PDGFr, FGFr) or non-receptor (e.g. c-src, lck, Zap70) kinases. Inappropriate or uncontrolled activation of many of these kinase, i.e. aberrant protein tyrosine kinase activity, for example by over-expression or mutation, has been shown to result in uncontrolled cell growth.

Aberrant activity of protein tyrosine kinases, such as c-erbB-2, c-src, c-met, EGFr and PDGFr have been implicated in human malignancies. Elevated EGFr activity has, for example, been implicated in non-small cell lung, bladder and head and neck cancers, and increased c-erbB-2 activity in breast, ovarian, gastric and pancreatic cancers. Inhibition of protein tyrosine kinases should therefore provide a treatment for tumours such as those outlined above.

Aberrant protein tyrosine kinase activity has also been implicated in a variety of other disorders: psoriasis, (Dvir et al, J.Cell.Biol; 1991, 113, 857–865), fibrosis, atherosclerosis, restenosis, (Buchdunger et al, Proc.Natl.Acad.Sci. USA; 1991, 92, 2258–2262), auto-immune disease, allergy, asthma, transplantation rejection (Klausner and Samelson, Cell; 1991, 64, 875–878), inflammation (Berkois, Blood; 1992, 79(9), 2446–2454), thrombosis (Salari et al, FEBS; 1990, 263(1), 104–108) and nervous system diseases (Ohmichi et al, Biochemistry, 1992, 31, 4034–4039). Inhibitors of the specific protein tyrosine kinases involved in these diseases eg PDGF-R in restenosis and EGF-R in psoriasis, should lead to novel therapies for such disorders. P56lck and zap 70 are indicated in disease conditions in which T cells are hyperactive e.g. rheumatoid arthritis, autoimmune disease, allergy, asthma and graft rejection. The process of angiogenesis has been associated with a number of disease states (e.g. tumourogenesis, psoriasis, rheumatoid arthritis) and this has been shown to be controlled through the action of a number of receptor tyrosine kinases (L. K. Shawver, DDT, 1997, 2(2), 50–63).

EP0635507 discloses a class of tricyclic quinazoline derivatives of the formula:

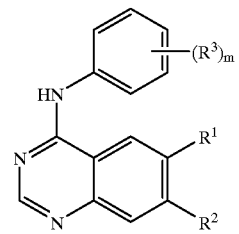

wherein $R^1$ and $R^2$ together form specified optionally substituted groups containing at least one heteroatom so as to form a 5 or 6-membered ring, in which there is a N atom at the 6 position of the quinazoline ring; $R^3$ includes independently hydrogen, hydroxy, halogeno, (1–4-C)alkyl, (1–4-C)alkoxy di-[(1–4-C)alkyl]amino, or (2–4C)alkanoylamino. The above citation notes that receptor tyrosine kinases in general, which are important in the transmission of biochemical signals initiating cell replication, are frequently present at increased levels or with higher activities in common human cancers such as breast cancer (Sainsbury et al, Brit. J. Cancer, 1988, 58, 458). It is suggested that inhibitors of receptor tyrosine kinases should be of value as inhibitors of the growth of mammalian cancer cells (Yaish et al. Science, 1988, 242, 933). This citation therefore has the aim of providing quinazoline derivatives which inhibit receptor tyrosine kinases involved in controlling the tumourigenic phenotype.

WO 95/15758 discloses aryl and heteroaryl quinazoline derivatives of formula

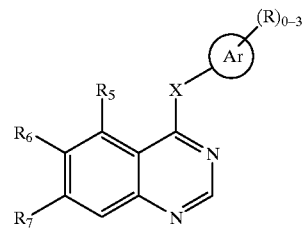

wherein X includes a bond, O, S, SO, $SO_2$, C≡C, C=C, $CH_2$ and NH; Ar includes phenyl, naphthyl, naphthalenyl, indolyl, pyridyl, piperidinyl, piperazinyl, dihydroquinolinyl, tetrahydroquinolinyl, thienyl, indanyl, pyrazolyl and 1,4-benzodioxanyl; and $R_5$, $R_6$ and $R_7$ independently include hydrogen, alkyl, alkylthio, cycloalkyl, hydroxy, alkoxy, aralkoxy, aryl, halo, haloalkyl, carboxy or carbalkoxy; as inhibitors of CSF-1R and/or p56lck receptor tyrosine kinase activity.

WO 95/19774 discloses bicyclic derivatives of formula:

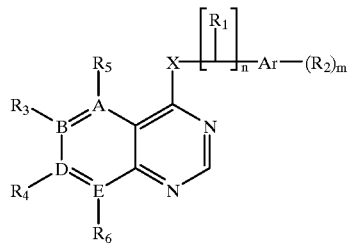

in which A to E are nitrogen or carbon and at least one of A to E is nitrogen; or two adjacent atoms together are N, O or S; $R_1$ is H or alkyl and n is 0, 1 or 2; m is 0 to 3 and $R_2$ includes optionally substituted alkyl, alkoxy, cycloalkoxy, cycloalkoxy, or two $R_2$ groups together form a carbocycle or heterocycle. The compounds are said to inhibit epidermal growth factor receptor tyrosine kinase and suggested uses include the treatment of cancer, psoriasis, kidney disease, pancreatitis and contraception.

WO 96/07657 discloses pyrimido[5,4-d]pyrimidine derivatives of formula

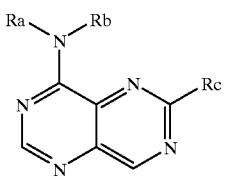

wherein Ra includes hydrogen or alkyl; Rb includes optionally substituted phenyl; and Rc includes hydrogen, halo, alkyl, cycloalkyl, cycloalkylalkylaryl, aralkyl, OH, optionally substituted alkoxy, cycloalkoxy, aryloxy, aralkoxy, mercapto, optionally substituted alkyl- or arylsulfenyl, -sulfinyl, or -suffonyl and substituted alkyleneimino; as EGF-R inhibitors.

WO 96/09294 discloses quinoline and quinazoline derivatives of formula

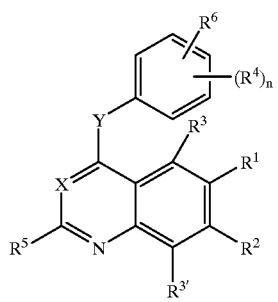

wherein X is N or CH; Y includes O, S, $CH_2O$ and NH; $R^6$ includes phenoxy, benzyloxy, benzylmercapto, benzylamino, benzyl, anilino, benzoyl, anilinocarbonyl, anilinomethyl, phenylethynyl, phenylethenyl, phenylethyl, phenylthio, phenylsulphonyl, benzylthio, benzylsulphonyl, phenylthiomethyl, phenylsulphonylmethyl, phenoxymethyl, thienylmethoxy, furanylmethoxy, cyclohexyl, and cyclohexylmethoxy; and $R^1$, $R^2$, $R^3$ and $R^{3'}$ include a range of possible substituents, predominantly not including heterocyclic ring systems; as protein receptor tyrosine kinase inhibitors, in particular as c-erbB-2 and/or p56lck inhibitors.

WO 96/15118 discloses quinazoline derivatives of formula

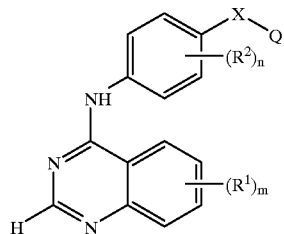

wherein X includes O, S, SO, $SO_2$, $CH_2$, $OCH_2$, $CH_2O$ and CO; Q includes a phenyl or naphthyl group and various 5- or 6-membered heteroaryl moieties; n is 0, 1, 2 or 3 and each $R^2$ is independently halogeno, trifluoromethyl, hydroxy, amino, nitro, cyano, $C_{1-4}$ alkyl, $C_{1-4}$ alkoxy, $C_{1-4}$ alkylamino, di$C_{1-4}$ alkyl amino or $C_{2-4}$ alkanoylamino; m is 1, 2 or 3 and $R^1$ includes a range of possible substituents, predominantly not including heterocyclic ring systems; as receptor tyrosine kinase inhibitors, in particular as EGF-R inhibitors.

WO 96/15128 discloses pyrido[2,3-d]pyrimidine and naphthyridine derivatives of formula

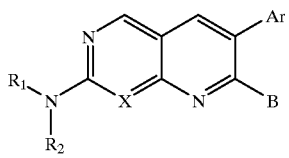

wherein X is CH or N; B is halo, hydroxy or $NR_3R_4$; Ar includes unsubstituted and substituted phenyl or pyridyl; and $R_1$, $R_2$, $R_3$ and $R_4$ independently include hydrogen, amino, $C_{1-8}$alkylamino, di-$C_{1-8}$alkylamino, unsubstituted and substituted aromatic or heteroaromatic groups, and unsubstituted and substituted $C_{1-8}$alkyl, $C_{2-8}$-alkenyl or $C_{2-8}$alkynyl groups.

WO 96/16960 discloses quinazoline derivatives of formula

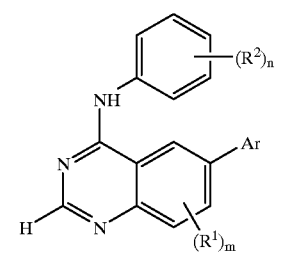

wherein m is 1 or 2; each $R^1$ independently includes hydrogen and $C_{1-4}$alkoxy; n is 1, 2 or 3; each $R^2$ independently includes hydrogen, halogeno and $C_{1-4}$alkyl, or $R^2$ is an aryl- or heteroaryl-containing group, including pyridylmethoxy and benzoyl; and Ar includes a substituted or unsubstituted 5 or 9-membered nitrogen-linked heteroaryl moiety containing up to four nitrogen atoms, in particular imidazol-1-yl, imidazolin-1-yl, benzimidazol-1-yl, pyrazol-1-yl and 1,2,4-triazol-1-yl; as receptor tyrosine kinase inhibitors, in particular as EGF-R inhibitors.

It is therefore a general object of the present invention to provide compounds suitable for the treatment of disorders mediated by protein tyrosine kinase activity, and in particular treatment of the above mentioned disorders.

In addition to the treatment of tumours, the present invention envisages that other disorders mediated by protein tyrosine kinase activity may be treated effectively by inhibition, including preferential inhibition, of the appropriate protein tyrosine kinase activity.

Broad spectrum inhibition of protein tyrosine kinase may not always provide optimal treatment of, for example tumours, and could in certain cases even be detrimental to subjects since protein tyrosine kinases provide an essential role in the normal regulation of cell growth.

It is another object of the present invention to provide compounds which preferentially inhibit protein tyrosine kinases, such as EGFr, c-erbB-2, c-erbB4, c-met, tie-2, PDGFr, c-src, lck, Zap70, and fyn. There is also perceived to be a benefit in the preferential inhibition involving small groups of protein tyrosine kinases, for example c-erbB-2 and c-erbB4 or c-erbB-2, c-erbB-4 and EGF-R.

A further object of the present invention is to provide compounds useful in the treatment of protein tyrosine kinase related diseases which minimise undesirable side-effects in the recipient.

The present invention relates to heterocyclic compounds which may be used to treat disorders mediated by protein tyrosine kinases and in particular have anti-cancer properties. More particularly, the compounds of the present invention are potent inhibitors of protein tyrosine kinases such as such as EGFr, c-erbB-2, c-erbB-4, c-met, tie-2, PDGFr, c-src, lck, Zap70, and fyn, thereby allowing clinical management of particular diseased tissues.

The present invention envisages, in particular, the treatment of human malignancies, for example breast, non-small cell lung, ovary, stomach, and pancreatic tumours, especially those driven by EGFr or erbB-2, using the compounds of the present invention. For example, the invention includes compounds which are highly active against the c-erbB-2 protein tyrosine kinase often in preference to the EGF receptor kinase hence allowing treatment of c-erB-2 driven tumours. However, the invention also includes compounds which are highly active against both c-erbB-2 and EGF-R receptor kinases hence allowing treatment of a broader range of tumours.

More particularly, the present invention envisages that disorders mediated by protein tyrosine kinase activity may be treated effectively by inhibition of the appropriate protein tyrosine kinase activity in a relatively selective manner, thereby minimising potential side effects.

Accordingly, the present invention provides a compound of formula (I):

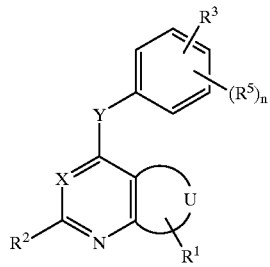

(I)

or a salt thereof;
wherein X is N or CH;
Y is a group W(CH$_2$), (CH$_2$)W, or W, in which W is O, S(O)$_m$ wherein m is 0, 1 or 2, or NR$^a$ wherein R$^a$ is hydrogen or a C$_{1-8}$ alkyl group;
R$^1$ represents a 5- or 6-membered heterocyclic ring containing 1 to 4 heteroatoms selected from N, O or S(O)$_m$, wherein m is as defined above, with the proviso that the ring does not contain two adjacent O or S(O)$_m$ atoms, the ring being substituted either (a) by one or more groups independently selected from carbamoyl, ureido, guanidino, C$_{5-8}$ alkyl, C$_{5-8}$ alkoxy, C$_{5-8}$ cycloalkoxyl, C$_{4-8}$alkylcycloalkoxy, C$_{5-8}$ alkylcarbonyl, C$_{5-8}$ alkoxycarbonyl, N—C$_{1-4}$ alkylcarbamoyl, N,N-di-[C$_{1-4}$ alkyl]carbamoyl, hydroxyamino, C$_{1-4}$ alkoxyamino, C$_{2-4}$ alkanoyloxyamino, phenyl, phenoxy, 4-pyridon-1-yl, pyrrolidin-1-yl, imidazol-1-yl, piperidino, morpholino, thiomorpholino, thiomorpholino-1-oxide, thiomorpholino-1,1-dioxide, piperazin-1-yl, 4-C$_{1-4}$ alkylpiperazin-1-yl, dioxolanyl, C$_{1-8}$ alkylthio, arylthio, C$_{1-4}$ alkylsulphinyl, C$_{1-4}$ alkylsulphonyl, arylsulphonyl, arylsulphinyl, halogeno-C$_{1-4}$ alkyl, hydroxy-C$_{1-4}$ alkyl, C$_{2-4}$ alkanoyloxy-C$_{1-4}$ alkyl, C$_{1-4}$ alkoxy-C$_{1-4}$ alkyl, carboxy-C$_{1-4}$ alkyl, formyl-C$_{1-4}$ alkyl, C$_{1-4}$ alkoxycarbonyl-C$_{1-4}$-alkylcarbamoyl-C$_{1-4}$ alkyl, N-C$_{1-4}$ alkylcarbamoyl-C$_{1-4}$alkyl, N,N-di-[C$_{1-4}$ alkyl]carbamoyl-C$_{1-4}$alkyl, amino-C$_{1-4}$ alkyl, C$_{1-4}$ alkylamino-C$_{1-4}$ alkyl, di-[C$_{1-4}$ alkyl]amino-C$_{1-4}$ alkyl, di-[C$_{1-4}$ alkyl]amino-C$_{1-4}$ alkylene-(C$_{1-4}$ alkyl)amino, C$_{1-4}$ alkylamino-C$_{1-4}$ alkylene-(C$_{1-4}$ alkyl)amino, hydroxy-C$_{1-4}$ alkylene-(C$_{1-4}$ alkyl)amino, phenyl-C$_{1-4}$ alkyl, 4-pyridon-1-yl-C$_{1-4}$ alkyl, pyrrolidin-1-yl-C$_{1-4}$ alkyl, imidazol-1-yl-C$_{1-4}$ alkyl, piperidino-C$_{1-4}$ alkyl, morpholino-C$_{1-4}$ alkyl, thiomorpholino-C$_{1-4}$ alkyl, thiomorpholino-1-oxide-C$_{1-4}$ alkyl, thiomorpholino-1,1-dioxide-C$_{1-4}$ alkyl, piperazin-1-yl-C$_{1-4}$ alkyl, 4-C$_{1-4}$ alkylpiperazin-1-yl-C$_{1-4}$ alkyl, hydroxy-C$_{2-4}$ alkoxy-C$_{1-4}$ alkyl, C$_{1-4}$ alkoxy-C$_{2-4}$ alkoxy-C$_{1-4}$ alkyl, hydroxy-C$_{2-4}$ alkylamino-C$_{1-4}$ alkyl, C$_{1-4}$ alkoxy-C$_{2-4}$ alkylamino-C$_{1-4}$ alkyl, C$_{1-4}$ alkylthio-C$_{1-4}$ alkyl, hydroxy-C2A alkylthiG-C$_{1-4}$ alkyl, C$_{1-4}$ alkoxy-C$_{2-4}$ alkylthio-C$_{1-4}$ alkyl, phenoxy-C$_{1-4}$ alkyl, anilino-C$_{1-4}$ alkyl, phenylthio-C$_{1-4}$ alkyl, cyano-C$_{1-4}$ alkyl, halogeno-C$_{2-4}$ alkoxy, hydroxy-C$_{2-4}$ alkoxy, C$_{2-4}$ alkanoyloxy-C$_{2-4}$ alkoxy, C$_{1-4}$ alkoxy-C$_{2-4}$ alkoxy, carboxy-C$_{1-4}$ alkoxy, formyl-C$_{1-4}$ alkoxy, C$_{1-4}$ alkoxycarbonyl-C$_{1-4}$ alkoxy, carbamoyl-C$_{1-4}$ alkoxy, N-C$_{1-4}$ alkylcarbamoyl-C$_{1-4}$ alkoxy, N,N-di-[C$_{1-4}$ alkyocarbamoyl-C$_{1-4}$ alkoxy, amino-C$_{2-4}$ alkoxy, C$_{1-4}$ alkylamino-C$_{2-4}$ alkoxy, di-[C$_{1-4}$ alkyl-C$_{2-4}$ alkoxy]amino-C$_{2-4}$ alkoxy, di-[C$_{1-4}$ alkyl]amino-C$_{2-4}$ alkoxy, C$_{2-4}$ alkanoyloxy, hydroxy-C$_{2-4}$ alkanoyloxy, C$_{2-4}$alkoxy-C$_{2-4}$ alkanoyloxy, phenyl-C$_{1-4}$ alkoxy, phenoxy-C$_{2-4}$ alkoxy, anilino-C$_{2-4}$ alkoxy, phenylthio-C$_{2-4}$ alkoxy, 4-pyridon-1-yl-C$_{2-4}$ alkoxy, piperidino-C$_{2-4}$ alkoxy, morpholino-C$_{2-4}$ alkoxy, thiomorpholino-C$_{2-4}$ alkoxy, thiomorpholino-1-oxide-C$_{2-4}$ alkoxy, thiomorpholino-1-oxide-C$_{2-4}$ alkoxy, piperazin-1-yl-C$_{2-4}$ alkoxy, 4-C$_{1-4}$ alkylpiperazin-1-yl-C$_{2-4}$ alkoxy, pyrrolidin-1-yl-C$_{2-4}$ alkoxy, imidazol-1-yl-C$_{2-4}$ alkoxy, halogeno-C$_{2-4}$ alkylamino, hydroxy-C$_{2-4}$ alkylamino, C$_{2-4}$ alkanoyloxy-C$_{2-4}$ alkylamino, C$_{1-4}$ alkoxy-C$_{2-4}$ alkylamino, carboxy-C$_{1-4}$ alkylamino, C$_{1-4}$ alkoxycarbonyl-C$_{1-4}$ alkylamino, carbamoyl-C$_{1-4}$ alkylamino, N-C$_{1-4}$ alkylcarbamoyl-C$_{1-4}$ alkylamino, N,N-di-[C$_{1-4}$ alkyl]carbamoyl. C$_{1-4}$ alkylamino, amino-C$_{2-4}$ alkylamino, C$_{1-4}$ alkylamino-C$_{2-4}$ alkylamino, di-[Cl4alkyl]amino-C$_{2-4}$ alkylamino, phenyl-C$_{1-4}$ alkylamino, phenoxy-C$_{2-4}$ alkylamino, anilino-C$_{2-4}$ alkylamino, 4-pyridon-1-yl-C$_{2-4}$ alkylamino, piperidino-C$_{2-4}$ alkylamino, morpholino-C$_{2-4}$ alkylamino, thiomorpholino-C$_{2-4}$ alkylamino, thiomorpholino-1-oxide-C$_{2-4}$ alkylamino, thiomorpholino-1,1-dioxide-C$_{2-4}$ alkylamino, piperazin-1-yl-C$_{2-4}$ alkylamino, 4-C$_{1-4}$ alkylpiperazin-1-yl-C$_{2-4}$ alkylamino, pyrrolidin-1-yl-C$_{2-4}$ alkylamino, imidazol-1-yl-C$_{2-4}$ alkylamino, phenylthio-C$_{2-4}$ alkylamino, C$_{2-4}$ alkanoylamino, C$_{1-4}$ alkoxycarbonylamino, C$_{1-4}$ alkylsulphonylamino, C$_{1-4}$ alkylsulphinylamino, benzamido, benzenesulphonamido, 3-phenylureido, 2-oxopyrrolidin-1-yl, 2,5-dioxopyrrolidin-1-yl, halogeno-$C_{2-4}$ alkanoylamino, hydroxy-$C_{2-4}$ alkanoylamino, hydroxy-$C_{2-4}$ alkanoyl-($C_{1-4}$ alkyl)-amino, $C_{1-4}$ alkoxy-$C_{2-4}$ alkanoylamino, carboxy-$C_{2-4}$ alkanoylamino, $C_{1-4}$ alkoxycarbonyl-$C_{2-4}$ alkanoylamino, carbamoyl-$C_{2-4}$ alkanoylamino, N-$C_{1-4}$ alkylcarbamoyl-$C_{2-4}$ alkanoylamino, N,N-di-[$C_{1-4}$ alkyl]carbamoyl-$C_{2-4}$ alkanoylamino, amino-$C_{2-4}$ alkanoylamino, $C_{1-4}$ alkylamino-$C_{2-4}$ alkanoylamino or di-[$C_{1-4}$ alkyl]amino-$C_{2-4}$ alkanoylamino; and wherein said benzamido or benzenesulphonamido substitutent or any anilino, phenoxy or phenyl group on an $R^1$ substituent may optionally bear one or two halogeno, $C_{1-4}$ alkyl or $C_{1-4}$ alkoxy substituents; and wherein any substituent containing a heterocyclic ring may optionally bear one or two halogeno, $C_{1-4}$ alkyl or $C_{1-4}$ alkoxy substituents on said ring; and wherein any substituent containing a heterocyclic ring may optionally bear one or two oxo or thioxo substituents on said ring; or (b) by one or more groups independently selected from $M^1$-$M^2$-$M^3$-$M^4$, $M^1$-$M^5$ or $M^1$-$M^2$-$M^{3'}$-$M^6$ wherein $M^1$ represents a $C_{1-4}$ alkyl group, wherein optionally a $CH_2$ group is replaced by a CO group;

$M^2$ represents $NR^{12}$ or $CR^{12}R^{13}$, in which $R^{12}$ and $R^{13}$ each independently represent H or $C_{1-4}$ alkyl;

$M^3$ represents a $C_{1-4}$ alkyl group;

$M^{3'}$ represents a $C_{1-4}$ alkyl group or is absent;

$M^4$ represents CN, $NR^{12}S(O)_mR^{13}$, $S(O)_mNR^{14}R^{15}$, $CONR^{14}R^{15}$, $S(O)_mR^{13}$ or $CO_2R^{13}$, in which $R^{12}$, $R^{13}$ and m are as hereinbefore defined and $R^{14}$ and $R^{15}$ each independently represent H or $C_{1-4}$ alkyl, or $R^{14}$ and $R^{15}$ together with the nitrogen atom to which they are attached represent a 5-or 6-membered ring optionally containing 1 or 2 additional heteroatoms selected from N, O or $S(O)_m$ in which ring any nitrogen atom present may optionally be substituted with a $C_{1-4}$ alkyl group, and which ring may optionally bear one or two oxo or thioxo substituents;

$M^5$ represents the group $NR^{14}R^{15}$, wherein $R^{14}$ and $R^{15}$ are as defined above, or $M^5$ represents the group

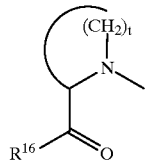

in which t represents 2 to 4 and $R^{16}$ represents OH, $OC_{1-4}$ alkyl or $NR^{14}R^{15}$; and $M^6$ represents a $C_{3-6}$ cycloalkyl group, the group $NR^{14}R^{15}$, wherein $R^{14}$ and $R^{15}$ are as defined above, or a 5- or 6-membered heterocyclic ring system containing 1 to 4 heteroatoms selected from N, O or S;

and $R^1$ is optionally further substituted by one or two halogeno, $C_{1-4}$ alkyl or $C_{1-4}$ alkoxy groups;

$R^2$ is selected from the group comprising hydrogen, halogen, trifluoromethyl, $C_{1-4}$ alkyl and $C_{1-4}$ as alkoxy;

each $R^5$ is independently selected from the group comprising hydrogen, hydroxy, halogen, $C_{1-4}$ alkyl, $C_{1-4}$ alkoxy, $C_{1-4}$ alkylamino, di-[$C_{1-4}$ alkyl]amino, $C_{1-4}$ alkylthio, $C_{1-4}$ alkylsulphinyl, $C_{1-4}$ alkylsulphonyl, $C_{1-4}$ alkylcarbonyl, $C_{1-4}$ alkylcarbamoyl, di-[$C_{1-4}$ alkyl] carbamoyl, carbamyl, $C_{1-4}$ alkoxycarbonyl, cyano, nitro and trifluoromethyl, and n is 1, 2 or 3;

$R^3$ is a group $ZR^4$ wherein Z is joined to $R^4$ through a $(CH_2)_p$ group in which p is 0, 1 or 2 and Z represents a group $V(CH_2)$, $V(CF_2)$, $(CH_2)V$, $(CF_2)V$, $V(CRR^1)$, $V(CHR)$ or V where R and R' are each $C_{1-4}$ alkyl and in which V is a hydrocarbyl group containing 0, 1 or 2 carbon atoms, carbonyl, dicarbonyl, CH(OH), CH(CN), sulphonamide, amide, O, $S(O)_m$ or $NR^b$ where $R^b$ is hydrogen or $R^b$ is $C_{1-4}$ alkyl; and $R^4$ is an optionally substituted $C_{3-6}$ cycloalkyl or an option ally substituted 5, 6, 7, 8, 9 or 10-membered carbocyclic or heterocyclic moiety; or $R^3$ is a group $ZR^4$ in which Z is $NR^b$, and $NR^b$ and $R^4$ together form an optionally

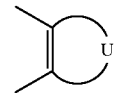

represents a fused 5, 6 or 7-membered heterocyclic ring containing 1 to 5 heteroatoms which may be the same or different and which are selected from N, O or $S(O)_m$, wherein m is as defined above, the heterocyclic ring containing a total of 1, 2 or 3 double bonds inclusive of the bond in the pyridine or pyrimidine ring, with the provisos that the heterocyclic ring does not form part of a purine and that the fused heterocyclic ring does not contain two adjacent O or $S(O)_m$ atoms.

Solvates of the compounds of formula (I) are also included within the scope of the present invention.

Heterocyclic groups comprise one or more rings which may be saturated, unsaturated, or aromatic and which may independently contain one or more heteroatoms in each ring.

Carbocyclic groups comprise one or more rings which may be independently saturated, unsaturated, or aromatic and which contain only carbon and hydrogen.

Suitably the 5, 6, 7, 8, 9 or 10-membered heterocyclic moiety is selected from the group comprising: furan, dioxolane, thiophene, pyrrole, imidazole, pyrrolidine, pyran, pyridine, pyrimidine, morpholine, piperidine, oxazole, isoxazole, oxazoline, oxazolidine, thiazole, isothiazole, thiadiazole, benzofuran, indole, isoindole, quinazoline, quinoline, isoquinoline and ketal.

Suitably the 5, 6, 7, 8, 9 or 10-membered carbocyclic moiety is selected from the group comprising: phenyl, benzyl, indene, naphthalene, tetralin, decalin, cyclopentyl, cyclopentenyl, cyclohexyl, cyclohexenyl and cycloheptyl.

By halo is meant fluoro, chloro, bromo or iodo.

Alkyl groups containing three or more carbon atoms may be straight, branched or cyclised.

In an embodiment $R^1$ is as defined above with the exception of wherein any substituent containing a heterocyclic ring bears one or two oxo or thioxo substituents on said ring; and $R^{14}$ and $R^{15}$ are as defined above with the exception of wherein they together with the nitrogen atom to which they are attached represent a 5- or 6membered ring and said ring bears one or two oxo or thioxo substituents; save that $R^1$ may represent a 5- or 6-membered heterocyclic ring substituted by a 4-pyridon-1-yl, 4-pyridon-1yl-$C_{1-4}$ alkyl, 4-pyridon-1-yl-$C_{2-4}$ alkoxy, 4-pyridon-1-yl-$C_{2-4}$ alkylamino, 2-oxopyrrolidin-1-yl or 2,5-dioxopyrrolidin-1-yl group.

In an embodiment, X is N.

In a further embodiment, Y is $NR^b$, $NR^b(CH_2)$, or $(CH_2)NR^b$; preferably Y is $NR^b$ and $R^b$ is preferably hydrogen or methyl.

In a further embodiment $R^1$ is a 5- or 6-membered heterocyclic ring as defined above substituted by one or more groups selected from dioxolanyl, hydroxy-$C_{1-4}$ alkyl, $C_{1-4}$ alkylamino-$C_{1-4}$ alkyl or di($C_{1-4}$-alkyl)amino-$C_{1-4}$ alkyl, and optionally further substituted by one or more $C_{1-4}$ alkyl groups.

In a preferred embodiment $R^1$ is a 5- or 6-membered heterocyclic ring as defined above substituted with a group selected from $M^1$- $M^2$-$M^3$-$M^4$, $M^1$-$M^5$ or $M^1$-$M^2$-$M^{3'}$-$M^6$ as defined above.

In a further embodiment the group $M^2$-$M^3$-$M^4$ represents an α-, β, or γ-amino carboxylic, sulphonic or suiphonic acid or a aralkyl ester, an amide or a $C_{1-4}$ alkyl- or di-($C_{1-4}$ alkyl)-amide thereof.

Preferably $M^1$ represents $CH_2$, CO, $CH_2CH_2$ or $CH_2CO$, more preferably $CH_2$.

Preferably $M^2$ represents $NR^{12}$ in which $R^{12}$ is as defined above; more preferably $R^{12}$ represents H or methyl.

Preferably $M^3$ represents $CH_2$, $CH_2CH_2$ or propyl.

Preferably $M^{3'}$ represents $CH_2$, ethyl, propyl, isopropyl or is absent.

Preferably $M^4$ represents $SOR^{13}$, $SOR^{13}$, $SO_2R^{13}$, $NR^{12}SO_2R^{13}$, $CO_2R^{13}$ or $CONR^{14}R^{15}$ in which $R^{12}$ and $R^{13}$ are defined above and $R^{14}$ and $R^5$ each independently represent H or $C_{1-4}$ alkyl; more preferably $R^{12}$, $R^{13}$, $R^{14}$ and $R^{15}$ each independently represent H or methyl.

Preferably $M^5$ represents a group $NR^{14}R^{15}$ in which $R^{14}$ and $R^{15}$ together with the nitrogen atom to which they are attached represent a 6-membered ring optionally containing an additional heteroatom selected from N or O, in which ring any nitrogen atom present may optionally be substituted with a $C_{1-4}$ alkyl group, preferably a methyl group; or $M^5$ represents a group

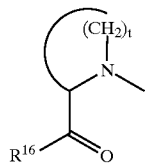

in which t represents 2 or 3 and $R^{16}$ represents OH, $NH_2$, $N(C_{1-4}$ alkyl$)_2$ or $C_{1-4}$ alkyl; more preferably $R^{16}$ represents $NH_2$ or $N(CH_3)_2$.

$M^5$ also preferably represents a group $NR^{14}R^{15}$ in which $R^{14}$ and $R^{15}$ each independently represent hydrogen or $C_{1-4}$ alkyl, more preferably hydrogen, methyl, ethyl or isopropyl.

Preferably $M^6$ represents a group $NR^{14}R^{15}$ in which $R^{14}$ and $R^{15}$ each independently represent $C_{1-4}$ alkyl, more preferably methyl, or $R^{14}$ and $R^{15}$ together with the nitrogen atom to which they are attached represent a 5- or 6-membered ring optionally containing an additional heteroatom selected from N or O, in which ring any nitrogen atom present may optionally be substituted with a $C_{1-4}$ alkyl group, preferably a methyl group; or $M^6$ represents a 5- or 6-membered heterocyclic ring system containing 1 or 2 heteroatoms selected from N or O.

In a further preferred embodiment $M^2$-$M^3$-$M^4$ represents an α-amino carboxylic acid or a methyl ester or amide thereof.

In a further preferred embodiment $M^2$-$M^3$-$M^4$ represents an α-, β- or γ-amino sulphinic or sulphonic acid, more preferably a β- or γ-amino sulphinic or sulphonic acid, most preferably a γ-aminosulphonic acid, or a methyl ester thereof.

In an especially preferred embodiment $M^2$-$M^3$-$M^4$ represents a methylsulphonylethylamino, methylsulphinylethylamino, methylsulphonylpropyiamino, methylsulphinylpropylamino, methylsulphonamidoethylamino, sarcosinamide, glycine, glycinamide, glycine methyl ester or acetylaminoethylamino group.

In a further especially preferred embodiment $M^5$ represents a piperazinyl, methylpiperazinyl, piperidinyl, prolinamido or N,N-dimethylprolinamido group.

In a further especially preferred embodiment $M^5$ represents an isopropylamino or N-morpholinyl group.

In a further especially preferred embodiment $M^1$-$M^5$ represents an isopropylacetamido or N-morpholinoacetamido group.

In a further especially preferred embodiment $M^2$-$M^3$-$M^6$ represents a pyridylamino, cyclopropylamino, N-(piperidin-4-yl)-N-methylamino, N,N-dimethylaminoprop-2ylamino, N-(2-dimethylaminoethyl)-N-ethylamino or tetrahydrofuranomethylamino group, preferably a pyridylamino group.

In an embodiment $R^1$ may be selected from the group comprising phenyl, furan, thiophene, pyridine, pyrimidine, pyrazine, pyrrole, oxazole, isoxazole, oxadiazole, thiazole, isothiazole, triazole, tetrazole and imidazole or a hydrogenated derivative of any of the aforementioned.

In a further preferred embodiment $R^1$ may be selected from the group comprising phenyl, furan, imidazole, tetrazole, triazole, pyrrolidine, piperazine, piperidine and oxadiazole.

In an especially preferred embodiment $R^1$ may be selected from the group comprising furan, imidazole and oxadiazole, most especially furan.

In an embodiment $R^2$ is hydrogen, $C_{1-4}$ alkyl, $C_{1-4}$ alkoxy or halogen, preferably hydrogen or methyl, more preferably hydrogen.

In a further embodiment, $R^5$ is hydrogen, hydroxy, $C_{1-4}$ alkyl, Ci- alkoxy, di[$C_{1-4}$ alkyl]amino, halogen, nitro or trifluoromethyl, preferably hydrogen, halogen or methyl, more preferably hydrogen.

In a preferred embodiment $R^4$ is an optionally substituted phenyl, dioxolanyl, thienyl, cyclohexyl or pyridyl group.

In a further embodiment Z is absent or represents oxygen, $CH_2$, $NR^1CH_2$, $CH_2NR^b$, $CH(CH_3)$, $OCH_2$, $CH(CN)$, $OCF_2$, $CH_2$, $CF_2O$, $SCH_2$, $S(O)_m$, carbonyl or dicarbonyl, wherein $R^b$ is hydrogen or $C_{1-4}$ alkyl.

In a preferred embodiment Z is oxygen, dicarbonyl, $OCH_2$, $CH(CN)$, $S(O)_m$ or $NR^b$, wherein $R^b$ is hydrogen or $C_{1-4}$ alkyl.

In a further preferred embodiment $R^3$ is benzyl, halo-, dihalo- and trihalobenzyl, α-methylbenzyl, phenyl, halo, dihalo- and trihalophenyl, pyridyl, pyridylmethyl, pyridyloxy, pyridylmethoxy, thienylmethoxy, dioxolanylmethoxy, cyclohexylmethoxy, phenoxy, halo-, dihalo- and trihalophenoxy, phenylthio, benzyloxy, halo-, dihalo- and trihalobenzyloxy, $C_{1-4}$ alkoxybenzyloxy, phenyloxalyl or benzenesulphonyl, more preferably benzyl, fluorobenzyl, benzyloxy, fluorobenzyloxy, pyridylmethyl, phenyl, benzenesulphonyl, phenoxy or fluorophenoxy.

In a further embodiment, $R^3$ is in the para position with respect to Y.

In a further embodiment, $(R^5)_n$ represents meta substituent(s) with respect to Y, and preferably n=1.

In a further embodiment,

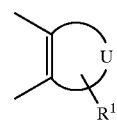

is selected from the group comprising:

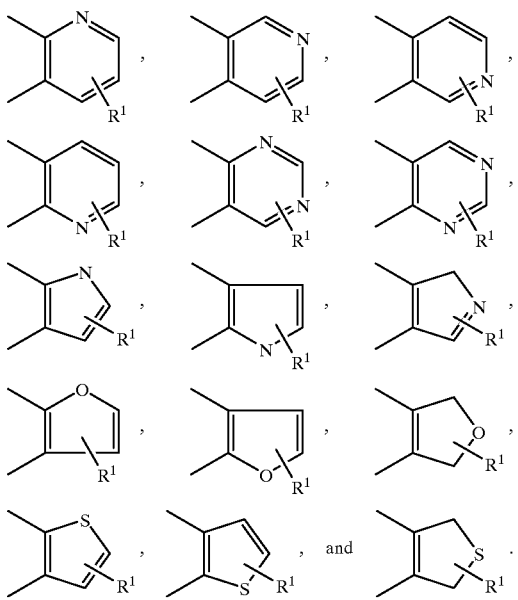

Preferably,

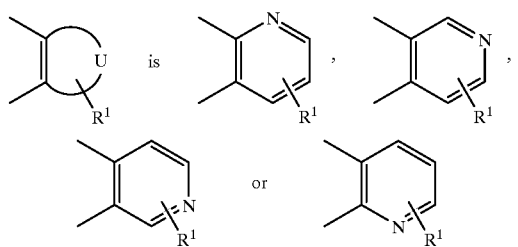

more preferably

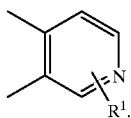

In an embodiment, the optional substituents for the carbocyclic or heterocyclic moiety, which may be present at any available position of said moiety, are selected from the group comprising:

$(CH_2)_qS(O)_m$—$C_{1-4}$ alkyl, $(CH_2)_qS(O)_m$—$C_{3-6}$cycloalkyl, $(CH_2)_qSO_2NR^8R^9$, $(CH_2)_qNR^8R^9$, $(CH_2)_qCO_2R^8$, $(CH_2)_qOR^8$, $(CH_2)_qCONR^8R^9$, $(CH_2)_qNR^8COR^9$, $(CH_2)_qCOR^8$, $(CH_2)_qR^8$, $NR^8SO_2R^9$ and $S(O)_mR^8$, wherein q is an integer from 0 to 4 inclusive; m is 0, 1 or 2;

$R^8$ and $R^9$ are independently selected from the group comprising hydrogen, $C_{1-4}$ alkyl, $C_{3-6}$ cycloalkyl, aryl, a 5- or 6-membered saturated or unsaturated heterocyclic ring which may be the same or different and which contains one or more heteroatoms which are selected from N, O or $S(O)_m$, with the proviso that the heterocyclic ring does not contain two adjacent O or $S(O)_m$ atoms.

In a further embodiment the optional substituents for the carbocyclic or heterocyclic moiety are selected from the group comprising morpholine, piperazine, piperidine, pyrrolidine, tetrahydrofuran, dioxolane, oxothiolane and oxides thereof, dithiolane and oxides thereof, dioxane, pyridine, pyrimidine, pyrazine, pyridazine, furan, thiofuran, pyrrole, triazine, imidazole, triazole, tetrazole, pyrazole, oxazole, oxadiazole and thiadiazole.

Other optional substituents for the carbocyclic or heterocyclic moiety and also for other optionally substituted groups include, but are not limited to, hydroxy, halogen, trifluoromethyl, trifluoromethoxy, nitro, amino, cyano, $C_{1-4}$ alkoxy, $C_{1-4}$ alkylthio, $C_{1-4}$ alkyl carbonyl, carboxylate and $C_{1-4}$ alkoxy carboxyl.

In a further embodiment X represents N; U represents a pyridine ring; and the group $R^1$ is in the 6-position of the pyridopyrimidine ring system.

In a preferred embodiment of the present invention there is provided a compound of formula (I) or a salt or solvate thereof wherein X represents N; U represents a pyridine ring; Y represents $NR^a$, wherein $R^a$ is hydrogen or $C_{1-4}$ alkyl; $R^1$ represents furan, thiophene, pyrrole, pyridine, pyrimidine, pyrazine, oxazole, isoxazole, oxadiazole, imidazole, tetrazole, triazole, dioxolane or a partially or fully hydrogenated derivative of any of these groups, preferably furan, oxadiazole or imidazole, substituted by one or more groups selected from hydroxy-$C_{1-4}$ alkyl, hydroxy-$C_{1-4}$ alkanoyl($C_{1-4}$ alkyl)amino, 1,3dioxolan-2-yl, $C_{1-4}$alkylamino-$C_{1-4}$alkyl or di($C_{1-4}$alkyl)amino-$C_{1-4}$alkyl, and optionally further substituted by one or more $C_{1-4}$alkyl groups; $R^2$ represents hydrogen; $R^5$ represents hydrogen or methyl; n is 1; and $R^3$ represents phenyl, benzyl, α-methylbenzyl, fluorobenzyl, benzenesulphonyl, phenoxy, fluorophenoxy, benzyloxy or fluorobenzyloxy.

In a further preferred embodiment of the present invention there is provided a compound of formula (I), or a salt or solvate thereof, wherein X represents N; U represents a pyridine ring; Y represents $NR^a$, wherein $R^a$ is hydrogen or $C_{1-4}$ alkyl; $R^1$ represents furan, thiophene, pyrrole, pyridine, pyrimidine, pyrazine, oxazole, isoxazole, oxadiazole, imidazole, tetrazole, thiazole, dioxolane or a partially or fully hydrogenated derivative of any of these groups, preferably furan, oxadiazole or imidazole, substituted by one or more groups selected from methylsulphonylethylaminomethyl, methylsulphonylethylamino-carbonyl, methylsulphinylethylamino-methyl, methylsulphinylethylamino-carbonyl, methylsulphonylpropylamino-methyl, methylsulphinylpropylamino-methyl, methylsulphonylpropyamino-carbonyl, methylsulphinylpropylamino-carbonyl, methylsulphonylethyl-(methylamino)-methyl, methylsulphonylethyl-(methylamino)-carbonyl, methylsulphinylethyl-(methylamino)methyl, methylsulphinylethyl-(methylamino)-carbonyl, methylsulphonylpropyl-(methylamino)methyl, methylsulphinylpropyl-(methylamino)methyl, methylsulphonylpropyl-(methylamino)-carbonyl, methylsulphinylpropyl-(methylamino)-carbonyl, methylsulphonamidoethylamino-methyl, methylsulphonamidopropylamino-methyl, sarcosinamidomethyl, glycinylmethyl, glycinamidomethyl, glycinylmethyl methyl ester, acetylaminoethylaminomethyl, piperazinylmethyl, methylpiperazinylmethyl, piperidinylmethyl, N-(prolinamido)methyl, (N,N-dimethylprolinamido)methyl, pyrdylaminomethyl, cyclopropylaminomethyl, N-(piperidin4-yl)N-methylaminomethyl, N,N-dimethylaminoprop-2-ylaminomethyl, N-(2-dimethylaminoethy)-N-ethylaminomethyl, isopropylacetamido, N-morpholinylacetamido or tetrahydrofuranomethylaminomethyl, and optionally further substituted by one or more $C_{1-4}$alkyl groups; $R^2$ represents hydrogen; $R^5$ represents hydrogen or methyl; n is 1; and $R^3$ represents phenyl, benzyl, α-methylbenzyl, fluorobenzyl, benzenesulphonyl, phenoxy, fluorophenoxy, benzyloxy or fluorobenzyloxy.

In an especially preferred embodiment of the present invention there is provided a compound of formula (I), or a salt thereof, wherein X represents N; U represents a pyridine ring; Y represents $NR^a$, wherein $R^a$ is hydrogen or $C_{1-4}$ alkyl; $R^1$ represents furan, oxadiazole or imidazole, preferably furan, substituted by a group selected from hydroxy-$C_{1-4}$ alkyl, 1,3-dioxolan-2-yl, $C_{1-4}$alkylamino-$C_{1-4}$alkyl or di($C_{1-4}$alkyl)amino-$C_{1-4}$alkyl, methylsulphonylethylaminomethyl, methylsulphinylethylaminomethyl, methylsulphonylpropylamino-methyl, methylsulphonylethyl-(methylamino)-methyl, methylsulphonamidoethylamino-methyl, sarcosinamidoethylmethyl, glycinylmethyl, glycinylmethyl methyl ester, acetylaminoethylaminomethyl, piperazinylmethyl, methylpiperazinylmethyl, piperidinylmethyl, N-(prolinamido)methyl, (N,N-dimethylprolinamido)methyl and pyrdylaminomethyl; $R^2$ represents hydrogen; $R^5$ represents hydrogen or methyl; n is 1; and $R^3$ represents fluorobenzyloxy, benzenesulphonyl or benzyloxy, preferably benzyloxy.

Preferred compounds of the present invention include:
- (4-Benzyloxy-phenyl-(6-(5-piperidin-1-ylmethyl)furan-2-yl)-pyrido[3,4-d]pyrimidin-4yl-amine;
- (4-Benzyloxy-phenyl-(6-(5-(4-methyl-piperazin-1-ylmethyl)-furan-2-yl)pyrido[3,4-d]pyrimidin-4-yl) amine;
- (4-Benzyloxy-phenyl-(6-(5-((2-methanesulphonyl-ethylamino)methyl)-furan-2-yl-pyrido[3,4-d] pyrimidin4-yl)-amine;
- ((5-(4-(4-Benzyloxy-phenylamino)-pyrido[3,4-d] pyrimidin-6-yl)-furan-2-ylmethyl)-amino)-acetic acid methyl ester;
- (4-Benzyloxy-phenyl)-(6-(5-(pyridin-3-ylaminomethyl)-furan-2-yl)pyrido[3,4-d]pyrimidin-4-yl)-amine;
- (4-Benzyloxy-phenyl)-6-(5-(dimethylaminomethyl)-furan-2-yl)-pyrido[3,4-d]pyrimidin-4-yl)-amine;
- (2S)-1-(5-(4-(4-Benzyloxy-phenylaminoypyrido)-pyrido[3,4-d]pyrimidine-6-yl)furan-2ylmethyl)-pyrrolidine-2-carboxylic acid amide;
- 2-((5-(4-(4-Benzyloxy-phenylamino)-pyrido[3,4-d] pyrimidin-6-yl)-furan-2-ylmethyl)-methylamino)-acetamide;
- N-(2-((5-(4-(4-Benzyloxy-phenylamino)pyrimido[3,4-d] pyrimidin-6-yl)-furan-2-ylmethyl)-amino)-ethyl)-acetamide;
- (4-Benzyloxy-phenyl(6-(5-((2-methanesulphinyl-ethylamino)-methyl)-furan-2-yl)-pyrido[3,4-d] pyrimidin-4-yl)-amine;
- ((5-(4-(4-Benzyloxy-phenylamino)pyrido[3,4-d] pyrimidine-6-yl)-furan-2-ylmethyl)-amino)-acetic acid;
- (5-(4-(4-Benzyloxy-phenylamino)-pyrido[3,4-d] pyrimidin-6-yl)-furan-2-yl-methanol;
- (2R)-1-{5-[4-(4-Benzyloxy-phenylamino)-pyrido[3,4-d] pyrimidin-6-yl]-furan-2-ylmethyl}-pyrrolidine-2-carboxylic acid amide;
- (4-Benzyloxy-phenyl)-(6-(5-((3-methanesulphonyl-propylamino)methyl)-furan-2-yl)-pyrido[3,4-d] pyrimidin-4-yl)-amine;
- (4-Benzyloxy-phenyl)-(6-(5-(((2-methanesulphonyl-ethyl)-methyl-amino)-methyl)furan-2-yl)-pyrido[3,4-d]pyrimidin-4-yl)-amine;
- (2S)-1-{5-[4-(4-Benzyloxy-phenylamino)pyrido[3,4-d] pyrimidin-6-yl]-furan-2-ylmethyl}-pyrrolidine-2-carboxylic acid dimethylamide;
- N-(2-((5-(4-(4-Benzyloxy-phenylamino)pyrido[3,4-d] pyrimidin-6-yl)-furan-2-ylmethyl)-amino)-ethyl)-methanesulphonamide;
- (4-Benzyloxyphenyl)-(6-(5-(1,3-dioxolan-2-yl-furan-2-yl-pyrido3,4-d]pyrimidine-4-yl)-amine;

and salts or solvates thereof, particularly pharmaceutically acceptable salts thereof.

Other preferred compounds of the present invention include:
- (4-Benzyloxy-phenyl)-(6-(5-(4-methyl-piperazin-1-ylmethyl)-N-methylimidazol-2-yl)-pyrido[3,4-d] pyrimidin-4-yl)-amine;
- (4-Benzyloxy-phenyl)-(6-(5-(dimethylaminomethyl)-N-methylimidazol-2-yl)-pyrido[3,4-d]pyrimidin-4-yl)-amine;
- (4-Benzyloxy-phenyl)-(6-(5-(4-methyl-piperazin-1-ylmethyl)-imidazol-2-yl)-pyrido[3,4-d]pyrimidin-4-yl)-amine;
- (4-Benzyloxy-phenyl)-(6-(5-(dimethylaminomethyl)-imidazol--2-yl)-pyrido[3,4-d]pyrimidin-4-yl)-amine;
- (4-Benzyloxy-phenyl)-(6-(1-4-methyl-piperazin-1-ylmethyl)-N-methylimidazol-2-yl)-pyrido[3,4-d] pyrimidin-4-yl)-amine;
- (4-Benzyloxy-phenyl)-(6-(1-(dimethylaminomethyl)-N-methylimidazol-2-yl)-pyrido[3,4-d]pyrimidin-4-yl)-amine;

and salts or solvates thereof, particularly pharmaceutically acceptable salts thereof.

Especially preferred compounds of the present invention include:
- (4-Benzyloxy-phenyl)-(6-(5-((2-methanesulphonyl-ethylaimino)methyl)-furan-2-yl)-pyrido[3,4-d] pyrimidin-4-yl)-amine;
- (2S)-1-(5-(4-(4-Benzyloxy-phenylamino)-pyrido[3,4-d] pyrimidine-6-yl)-furan-2-ylmethyl)-pyrrolidine-2-carboxylic acid amide;
- (2R)-1-{-[4-(4-Benzyloxy-phenylamino)pyrido[3,4-d] pyrimidin-6-yl]-furan-2-ylmethy}-pyrrolidine-2-carboxylic acid amide;
- (2S)-1-{-5-[4-(4-Benzyloxy-phenylamino)-pyrido[3,4-d] pyrimidin-6-yl]-furan-2ylmethyl}-pyrrolidine-2-carboxylic acid dimethylamide;

and salts or solvates thereof, particularly pharmaceutically acceptable salts thereof.

Certain compounds of formula (I) may exist in stereoisomeric forms (e.g. they may contain one or more asymmetric carbon atoms or may exhibit cis-trans isomerism).

The individual stereoisomers (enantiomers and diastereoisomers) and mixtures of these are included within the scope of the present invention. Likewise, it is understood that compounds of formula (I) may exist in tautomeric forms other than that shown in the formula and these are also included within the scope of the present invention.

Salts of the compounds of the present invention may comprise acid addition salts derived from a nitrogen in the compound of formula (I). The therapeutic activity resides in the moiety derived from the compound of the invention as defined herein and the identity of the other component is of less importance although for therapeutic and prophylactic purposes it is, preferably, pharmaceutically acceptable to the patient. Examples of pharmaceutically acceptable acid addition salts include those derived from mineral acids, such as hydrochloric, hydrobromic, phosphoric, metaphosphoric, nitric and sulphuric acids, and organic acids, such as tartaric, acetic, trifluoroacetic, citric, malic, lactic, fumaric, benzoic, glycolic, gluconic, succinic and methanesulphonic and arylsulphonic, for example Q-toluenesulphonic, acids.

According to a further aspect of the present invention there is provided a process for the preparation of a compound of formula (I) as defined above which comprises the steps:

(a) the reaction of a compound of formula (II)

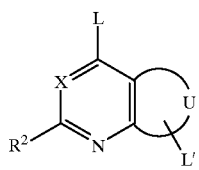
(II)

wherein U, X and $R^2$ are as defined above and L and L' are suitable leaving groups, with a compound of formula (III)

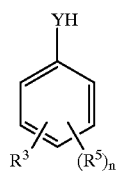
(III)

wherein Y, $R^3$, $R^5$ and n are as defined above, to prepare a compound of formula (IV)

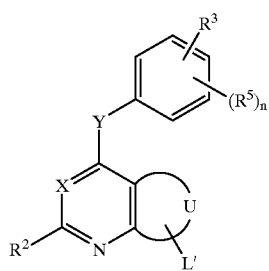
(IV)

and subsequently (b) reaction with an appropriate reagent to substitute the group $R^1$ onto the ring U by replacement of the leaving group $L^{40}$; and, if desired, (c) subsequently converting the compound of formula (I) thereby obtained into another compound of formula (I) by means of appropriate reagents.

Alternatively, the compound of formula (II) as defined above is reacted with the appropriate reagent to substitute the group $R^1$ onto the ring U by replacement of the leaving group L' and then the product thereby obtained (of formula (V) below) is reacted with the compound of formula (III) as defined above, followed, if desired, by conversion of the compound of formula (I) thereby obtained into another compound of formula (I).

In a variant of this alternative the compound of formula (V)

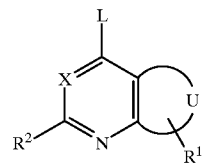
(V)

may be prepared by the reaction of a compound of formula (VI)

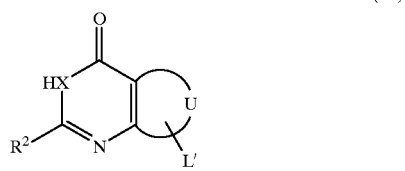
(VI)

with an appropriate reagent to substitute the group $R^1$ onto the ring U to prepare a compound of formula (VII)

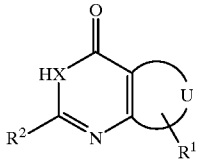
(VII)

and subsequent reaction to incorporate the leaving group L. For example, a chloro leaving group can be incorporated by reaction of a corresponding 3,4-dihydropyrimidone with carbon tetrachloride/triphenylphosphine in an appropriate solvent.

The group $R^1$ may, therefore, be substituted onto the ring U by replacement of a suitable leaving group. This is especially suitable for preparing compounds where $R^1$ is a substituted or unsubstituted heterocyclic ring system; such compounds may, for example, be prepared by reaction of the corresponding heteroaryl stannane derivative with the corresponding compound of formula (IV) carrying the leaving group L' in the appropriate position on the ring.

The reagent used to effect the substitution of the group $R^1$ onto the ring U may, in certain circumstances, include appropriate protecting group(s) well known to the person skilled in the art for particular functionalities. This may, for example, be suitable where the group $R^1$ contains a free amino functionality. Such protecting group(s) would be removed by standard methods after the substitution onto the ring U has been effected. For a description of protecting groups and their use see T. W. Greene and P. G. M. Wuts, "Protective Groups in Organic Synthesis", 2nd edn., John Wiley & Sons, New York, 1991.

According to a further aspect of the present invention there is provided a process for the preparation of a compound of formula (I) as defined above which comprises the steps:

(a) reacting a compound of formula (IV) as defined above with appropriate reagent(s) to prepare a compound wherein the group L' is replaced with an appropriately functionalised group Z;

and (b) subsequently converting the group Z into the group $R^1$ by means of appropriate reagent(s);

and, if desired, (c) subsequently converting the compound of formula (I) thereby obtained into another compound of formula (I) by means of appropriate reagents.

Such processes are particularly suitable for the preparation of compounds of formula (I) wherein $R^1$ carries a substituent selected from $M^1$-$M^2$-$M^3$-$M^4$, $M^1$-$M^5$ or $M^1$-$M^2$-$M^3$-$M^6$ as defined above in which $M^2$ represents $NR^{12}$. In such cases preferably the group Z carries a terminal formyl group (CHO).

Where Z carries a formyl group the compound may be suitably prepared from the corresponding dioxolanyl substituted compound, for example by acid hydrolysis. The dioxolanyl substituted compound may be prepared by reaction of a compound of formula (IV) with an appropriate reagent to substitute the leaving group L' with the substituent carrying the dioxolanyl ring. This reagent could, for example, be an appropriate heteroaryl stannane derivative.

Where Z carries a terminal formyl group the compound could suitably be prepared by reaction of a compound of formula (IV) with an appropriate heteroaryl stannane derivative. This derivative is either readily available or can be readily synthesised by those skilled in the art using conventional methods of organic synthesis. Suitable For the preparation of those compounds wherein in $M^1$ the $CH_2$ group adjacent to $M^2$ is replaced with a CO group a suitable process would comprise reaction of a compound in which the group Z carries a —($C_{0-3}$ alkylene)-$CO_2H$ group with a compound of formula $HM^2$-$M^3$-$M^4$, a compound of formula $HM^2$-$M^{3'}$-$M^6$ or a compound of formula $HM^5$, wherein $M^2$ represents $NR^{12}$.

Alternatively, an analogous scheme to those described above could be used wherein the substitution of the group $R^1$ onto the ring U occurs prior to the coupling reaction with the compound of formula (III).

According to a further alternative process the group Z is converted into the group $R^1$ by a de novo synthesis of the substituted or unsubstituted heterocyclic ring system using appropriate reagents. Such a process would involve standard synthetic methodology known to the person skilled in the art for building up the heterocyclic ring system.

For example, Z could suitably represent an alkyne group which when reacted with an appropriate nitrile oxide results in the formation of an isoxazole ring system; reaction with an azide would result in the formation of a triazole ring system. The group Z could also suitably represent an amidoxime group (derived from a cyano group) which when possibilities include the following schematic examples:-

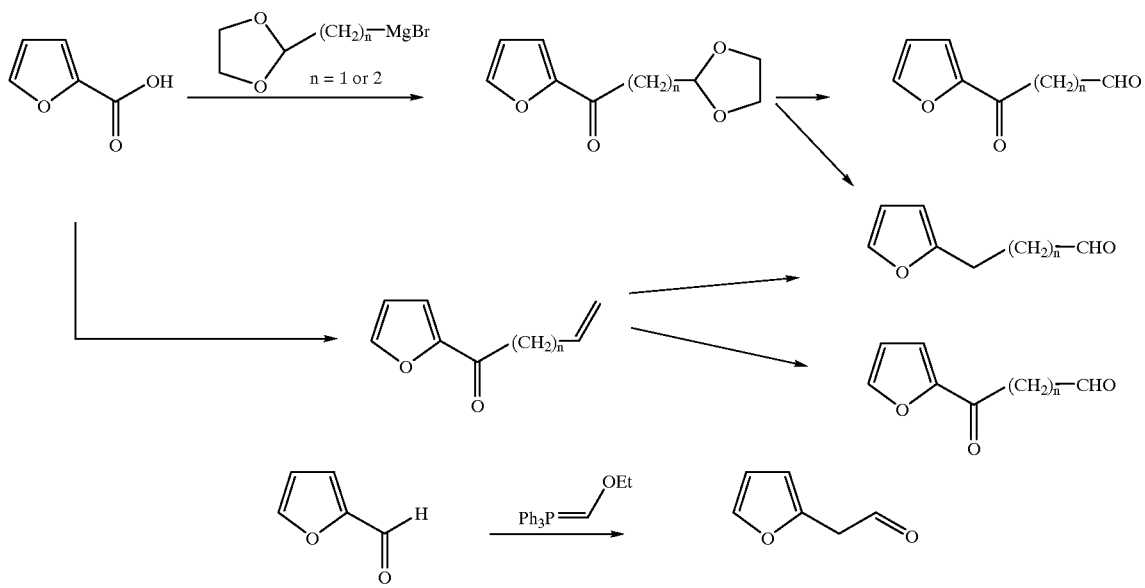

The resulting compounds would, for example, then be converted into the respective stannane derivative.

Analogous methods could be used for other heterocyclic ring systems.

Therefore a suitable process may comprise reaction of the compound in which the group Z carries a terminal formyl group (i.e. a —CHO or —($C_{1-3}$ alkylene)-CHO group) with a compound of formula $HM^2$-$M^3$-$M^4$, a compound of formula $HM^2$-$M^{3'}$-$M^6$ or a compound of formula $HM^5$, wherein $M^2$ represents $NR^{12}$. The reaction preferably involves a reductive amination by means of an appropriate reducing agent, for example sodium triacetoxyborohydride.

A similar process would be involved where in $M^1$ one $CH_2$ group was replaced with a CO group and $M^2$ was $NR^{12}$. If necessary, in certain circumstances, the ketone could be protected by standard methods to ensure that the reductive animation involved the aldehyde functionality.

reacted with an activated carboxylic acid derivative (such as an acid chloride or an acid imidazolide) would result in the formation of a 1,2,4-oxadiazole ring system. The group Z could also suitably represent a bromomethylenecarbonyl group which would be reacted with an imidate to result in the formation of an oxazole ring system, with a guanidino group to result in the formation of an N-imidazole ring system or with an amidine group to result in the formation of a C-imidazole ring system. The group Z could also suitably represent an activated carboxylic acid group which would be reacted to form a hydrazinoketone which would subsequently be reacted with another activated carboxylic acid derivative to result in the preparation of a 1,3,4-oxadiazole ring system. Thus reaction of a compound carrying a relevant Z group with appropriate reagents carrying one of —C≡N=O, —NH—C($NH_2$)=NH, —COX, —C($NH_2$)=NOH, —C(OMe)=NH, or —C($NH_2$)=NH as a terminal group would result in the formation of the ring systems indicated above.

Alternatively, an analogous scheme to those described above could be used wherein the substitution of the group $R^1$ onto the ring U occurs prior to the coupling reaction with the compound of formula (III).

The following scheme outlines, for example, the synthesis of derivatives carrying a substituted 1,3,4-oxadiazole ring as an $R^1$ substituent:

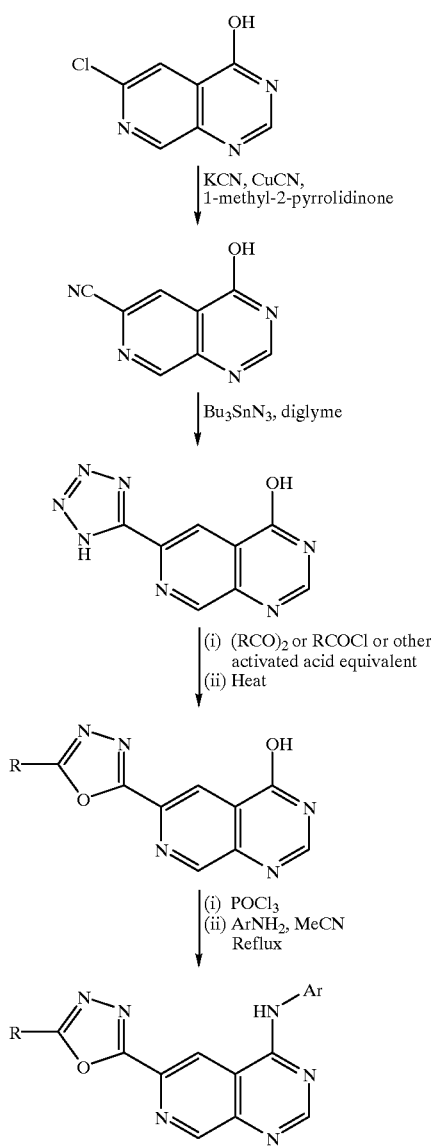

Such processes are particularly suitable for the preparation of the compounds of formula (I) wherein the compounds carry a substituent selected from $M^1$-$M^2$-$M^3$-$M^4$, $M^1$-$M^5$ or $M^{3'}$-$M^2$-$M^3$-$M^6$ as defined above in which $M^2$ represents $CR^{12}R^{13}$, including those in which in $M^1$ one $CH_2$ group is replaced by a CO group.

Suitable leaving groups for L and L' will be well known to those skilled in the art and include, for example, halo such as chloro and bromo; sulphonyloxy groups such as methanesulphonyloxy and toluene-p-sulphonyloxy; alkoxy groups; and triflate.

The coupling reaction referred to above with the compound of formula (III) is conveniently carried out in the presence of a suitable inert solvent, for example a $C_{1-4}$ alkanol, such as isopropanol, a halogenated hydrocarbon, an ether, an aromatic hydrocarbon or a dipolar aprotic solvent such as acetone or acetonitrile at a non-extreme temperature, for example from 0 to 150°, suitably 10 to 100° C., preferably 50 to 100° C.

Optionally, the reaction is carried out in the presence of a base when Y=NH. Examples of suitable bases include an organic amine such as triethylamine, or an alkaline earth metal carbonate, hydride or hydroxide, such as sodium or potassium carbonate, hydride or hydroxide. When YH=OH or SH it is necessary to perform the reaction in the presence of a base, and in such a case the product is not obtained as the salt.

The compound of formula (I) in the case in which $Y=NR^b$ may be obtained from this process in the form of a salt with the acid HL, wherein L is as hereinbefore defined, or as the free base by treating the salt with a base as hereinbefore defined.

The compounds of formulae (II) and (III) as defined above, the reagent to substitute the group $R^1$ and the reagent(s) to convert the group Z into the group $R^1$ are either readily available or can be readily synthesised by those skilled in the art using conventional methods of organic synthesis.

As indicated above, the compound of formula (I) prepared may be converted to another compound of formula (1) by chemical transformation of the appropriate substituent or substituents using appropriate chemical methods (see for example, J. March "Advanced Organic Chemistry", Edition III, Wiley Interscience, 1985).

For example, a compound containing an alkyl or aryl mercapto group may be oxidised to the corresponding sulphinyl or sulphonyl compound by use of an organic peroxide (eg benzoyl peroxide) or suitable inorganic oxidant (eg OXONE®).

A compound containing a nitro substituent may be reduced to the corresponding amino-compound, eg by use of hydrogen and an appropriate catalyst (if there are no other susceptible groups) or by use of Raney Nickel and hydrazine hydrate.

Amino or hydroxy substituents may be acylated by use of an acid chloride or an anhydride under appropriate conditions. Equally an acetate or amide group may be cleaved to the hydroxy or amino compound respectively by treatment with, for example, dilute aqueous base.

In addition reaction of an amino substituent with triphosgene and another amine (eg aqueous ammonia, dimethylamine) gives the urea substituted product.

An amino substituent may also be converted to a dimethylamino substituent by reaction with formic acid and sodium cyanoborohydride.

A formyl substituent may be converted to a hydroxymethyl or a carboxy substituent by standard reduction or oxidation methods respectively.

All of the above-mentioned chemical transformations may also be used to convert one compound of formula (II) to a further compound of formula (II) prior to any subsequent reaction; or to convert one compound of formula (III) to a further compound of formula (III) prior to any subsequent reaction.

Various intermediate compounds used in the above-mentioned processes, including but not limited to certain of the compounds of formulae (II), (III), (IV), (V), (VI) and (VII) as illustrated above, are novel and thus represent a further aspect of the present invention.

The compounds of formula (I) and salts thereof have anticancer activity as demonstrated hereinafter by their inhibition of the protein tyrosine kinase c-erbB-2, c-erbB4 and/or EGF-r enzymes and their effect on selected cell lines whose growth is dependent on c-erbA2 or EGF-r tyrosine kinase activity.

The present invention thus also provides compounds of formula (I) and pharmaceutically acceptable salts or solvates thereof for use in medical therapy, and particularly in the treatment of disorders mediated by aberrant protein tyrosine kinase activity such as human malignancies and the other disorders mentioned above. The compounds of the present invention are especially useful for the treatment of disorders caused by aberrant c-erbB-2 and/or EGF-r activity such as breast, ovarian, gastric, pancreatic, non-small cell lung, bladder, head and neck cancers, and psoriasis.

A further aspect of the invention provides a method of treatment of a human or animal subject suffering from a disorder mediated by aberrant protein tyrosine kinase activity, including susceptible malignancies, which comprises administering to said subject an effective amount of a compound of formula (I) or a pharmaceutically acceptable salt or solvate thereof.

A further aspect of the present invention provides the use of a compound of formula (I), or a pharmaceutically acceptable salt or solvate thereof, in therapy.

A further aspect of the present invention provides the use of a compound of formula (I), or a pharmaceutically acceptable salt or solvate thereof, in the preparation of a medicament for the treatment of cancer and malignant tumours.

A further aspect of the present invention provides the use of a compound of formula (I), or a pharmaceutically acceptable salt thereof, in the preparation of a medicament for the treatment of psoriasis.

Whilst it is possible for the compounds, salts or solvates of the present invention to be administered as the new chemical, it is preferred to present them in the form of a pharmaceutical formulation.

According to a further feature of the present invention there is provided a pharmaceutical formulation comprising at least one compound of formula (I), or a pharmaceutically acceptable salt or solvate thereof, together with one or more pharmaceutically acceptable carriers, diluents or excipients.

Pharmaceutical formulations may be presented in unit dose forms containing a predetermined amount of active ingredient per unit dose. Such a unit may contain for example 0.5 mg to 1 g, preferably 70 mg to 700 mg, more preferably 5 mg to 100 mg of a compound of the formula (I) depending on the condition being treated, the route of administration and the age, weight and condition of the patient.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may include other agents conventional in the art having regard to the type of formulation in question, for example those suitable for oral administration may include flavouring agents.

The animal requiring treatment with a compound, salt or solvate of the present invention is usually a mammal, such as a human being.

A therapeutically effective amount of a compound, salt or solvate of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of the present invention for the treatment of neoplastic growth, for example colon or breast carcinoma will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate of the present invention may be determined as a proportion of the effective amount of the compound per se.

The compounds of the present invention and their salts and solvates may be employed alone or in combination with other therapeutic agents for the treatment of the above-mentioned conditions. In particular, in anti-cancer therapy, combination with other chemotherapeutic, hormonal or antibody agents is envisaged. Combination therapies according to the present invention thus comprise the administration of at least one compound of formula (I) or a pharmaceutically acceptable salt or solvate thereof and at least one other pharmaceutically active agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect.

Certain embodiments of the present invention will now be illustrated by way of example only. The physical data given for the compounds exemplified is consistent with the assigned structure of those compounds.

$^1$H NMR spectra were obtained at 250 MHz on a Bruker AC250 or Bruker AM$^{250}$ spectrophotometer. J values are given in Hz. Mass spectra were obtained on one of the following machines: VG Micromass Platform (electrospray positive or negative) or HP5989A Engine (thermospray positive). Analytical thin layer chromatography (tlc) was used to verify the purity of some intermediates which could not be isolated or which were too unstable for full characterisation, and to follow the progress of reactions. Unless otherwise stated, this was done using silica gel (Merck Silica Gel 60 F254). Unless otherwise stated, column chromatography for the purification of some compounds used Merck Silica gel 60 (Art. 1.09385, 230–400 mesh), and the stated solvent system under pressure. Petrol refers to petroleum ether, either the fraction boiling at 40–60° C., or at 60–80° C. Ether refers to diethylether. DMAP refers to 4-dimethylaminopyridine. DMF refers to dimethylformamide. DMSO refers to dimethylsulphoxide. IMS refers to industrial methylated spirit. THF refers to tetrahydrofuran. TMEDA refers to N,N,N',N'-tetramethylethylenediamine. HPLC refers to high pressure liquid chromatography. RT refers to retention time.

Useful preparative techniques are described in WO96/09294, WO97/03069 and WO97/13771; also described in these publications are appropriate intermediate compounds other than those detailed below.

General Procedures

A/ Reaction of an amine with a bicyclic species containing a 4-chloro pyrimidine ring.

The optionally substituted bicyclic species and the specified amine were mixed in an appropriate solvent and heated to reflux. When the reaction was complete (as judged by tlc), the reaction mixture was allowed to cool. The resulting suspension was diluted e.g. with acetone and the solid collected by filtration, washing e.g. with excess acetone, and dried at 60° C. in vacuo.

B/ Reaction of product of A/ with a heteroaryl tin reagent.

A stirred mixture of the product of A/, e.g. a chloropyridopyrimidine, a heteroaryl stannane and a suitable palladium catalyst, such as bis-(triphenylphosphine) palladium (II) chloride or 1,4-bis(diphenylphosphino)-butane palladium (II) chloride (prepared as described in C. E. Housecraft et. al, lnorg. Chem. (1991), 30(1), 125–30), together with other appropriate additives, were heated at reflux in dry dioxane or another suitable solvent under nitrogen until the reaction was complete. The dark mixture was purified by chromatography on silica eluting with ethyl acetate/methanol mixtures.

Preparation Of Intermediates

4-Benzyloxyaniline is commercially available as the hydrochloride salt; this is treated with aqueous sodium carbonate solution, and the mixture extracted with ethyl acetate; the organic solution is dried (MgSO$_4$) and concentrated to give the free base as a brown solid, used without further purification.

Other substituted anilines were in general prepared by analogous methods to those outlined in WO 96/09294 and/or as follows:

Step 1: Preparation of the precursor nitro-compounds

4-Nitrophenol (or an appropriate substituted analogue, such as 3-chloro4-nitrophenol) was treated with a base such as potassium carbonate or sodium hydroxide in an appropriate solvent, such as acetone or acetonitrile. The appropriate aryl or heteroaryl halide was added and the reaction mixture heated or stirred at room temperature overnight.

Purification A: Most of the acetonitrile was removed in vacuo, and the residue was partitioned between water and dichloromethane. The aqueous layer was extracted with further dichloromethane (×2), and the combined dichloromethane layers were concentrated in vacuo.

Purification B: removal of insoluble material by filtration, followed by concentration of the reaction mixture in vacuo, and chromatography on silica.

Step 2: Reduction to the corresponding aniline

The precursor nitro compound was reduced by catalytic hydrogenation at atmospheric pressure using 5%Pt/carbon, in a suitable solvent (eg ethanol, THF, or mixtures thereof to promote solubility). When reduction was complete, the mixture was filtered through Harborlite™, washing with excess solvent, and the resulting solution concentrated in vacuo to give the desired aniline. In some cases, the anilines were acidified with HCl (e.g. in a solution in dioxane) to give the corresponding hydrochloride salt.

Anilines prepared by such methods include:

4-(2-Fluorobenzyloxy)aniline; m/z (M+1)$^+$218
4-(3-Fluorobenzyloxy)aniline; m/z (M+1)$^+$218
4-(4-Fluorobenzyloxy)aniline; m/z (M+1)$^+$218
3-Chloro-4-(2-fluorobenzyloxy)aniline; m/z (M+1)$^+$252
3-Chloro-4-(3-fluorobenzyloxy)aniline; m/z (M+1)$^+$252
3-Chloro-4-(4-fluorobenzyloxy)aniline; m/z (M+1)$^+$252
4-(Pyridyl-2-methoxy)aniline; m/z (M+1)$^+$201
4-(Pyridyl-4-methoxy)aniline; m/z (M+1)$^+$201
4-(Pyridyl-3-methoxy)aniline; m/z (M+1)$^+$201
4-Benzyloxy-3-chloroaniline; m/z (M+1)$^+$234 and, in appropriate cases, their hydrochloride salts.

4-Benzenesulghonylaniline was prepared by the published method (Helv. Chim. Acta., 1983, 66(4), p1046.

N-5-[N-tert-butoxycarbonyl)amino]-2-chloropyridine

A stirred solution of 6-chloronicotinic acid (47.3 g), diphenylphosphoryl azide (89.6 g) and triethylamine (46 ml) in t-butanol (240 ml) were heated under reflux under nitrogen for 2.5 hours. The solution was cooled and concentrated in vacuo. The syrupy residue was poured into 3 litres of a rapidly stirred solution of 0.33N aqueous sodium carbonate. The precipitate was stirred for one hour and filtered. The solid was washed with water and dried in vacuo at 70° C. to give the title compound (62 g) as a pale brown solid, m.p. 144–146° C.: δH [$^2$H$_6$]-DMSO 8.25 (1H,d), 7.95 (1H, bd), 7.25 (1H, d), 6.65 (1H, bs), 1.51 (9H,s); m/z (M+1)$^+$229.

This material may subsequently be carried forward to the appropriately substituted pyridopyrimidine intermediate according to the procedures as described in WO95/19774, J. Med. Chem., 1996, 39, pp 1823–1835, and J. Chem. Soc., Perkin Trans. 1, 1996, pp 2221–2226. Specific compounds made by such procedures include 6-chloro-pyrido[3,4-d] pyrimidin-one and 4,6-dichloropyrido[3,4-d]pyrimidine.

(4-Benzyloxy-phenyl)(6-chloro-pyrido[3,4-d]pyrimidin-4-yl)-amine

Prepared according to Procedure A from 4-benzyloxyaniline and 4,6-dichloropyrido[3,4-d] pyrimidine; δH (CDCl$_3$) 9.11 (1H,s), 8.78 (1H,s), 7.75 (1H,d), 7.56 (2H,dd), 7.40 (5H,m), 7.15 (2H,d), 5.10 (2H,s); m/z (M+1)$^+$409.

5-(4-(4-Benzloxy-phenylamino)-pyrido[(3,4-d] pyrimidin-6-yl)-furan-2-carbaldehyde (4-Benzyloxyphenyl-(6-chloro-pyrido[3,4-d]pyrimidin4-ylyamine (4.0 g, 11.0 mmol), 5-(1,3-dioxolan-2-yl)-2-(tributylstannyl)furan (J. Chem. Soc., Chem Commun., (1988), 560) (6.0 g, 14.0 mmol) were reacted together in a procedure analogous to Procedure B above for 20 hrs. The reaction mixture was allowed to cool, 1 N HCl (50 ml) added and stirred at room temperature for 15 minutes. The reaction was filtered and the residue washed with dioxane (20 ml) and 2N HCl (20 ml). The combined filtrate and washings were stirred at room temperature for a further hour. The dioxane was removed under vacuum, the reaction diluted with water and the solid which precipitated was collected by filtration, and washed with water, isohexane and acetone. This precipitate was converted to the free base by partitioning into a mixture of triethylamine, ethyl acetate and water. The organic phase was washed with water, dried (magnesium sulphate) and the solvent removed under vacuum. The residue was triturated with iso-hexane/ethyl acetate to give the product (2.41 g, 52%) as a yellow solid; δH [$^2$H$_6$]-DMSO 10.60 (1H, b, NH), 9.83 (1H, s, CHO), 9.30 (1H, s, 2-H), 9.08 (1H, s, 5-H or 8-H), 8.76 (1H, s, 5-H or 8-H), 7.89 (1H, d, furan-H), 7.82 (2H, d, 2'-H, 6'-H), 7.65–7.42 (6H, m, 5× Ph-H, furan-H), 7.21 (2H, d, 3'-H, 5'-H), 5.26 (2H, s, OCH$_2$); m/z (M +1)$^+$423.

N-Methyl-N-(2-methanesulphonyl-ethyl)amine hydrochloride

Methylvinyl sulphone (2.1 g, 19.78 mmol) and methylamine (33% solution in IMS, 40 ml, excess) were mixed and heated at reflux under a nitrogen atmosphere for 6 hours. After standing overnight at room temperature, the mixture was concentrated in vacuo to give a yellow oil, which was treated with ethereal HCl to give a sticky solid. Trituration with absolute ethanol gave the title compound as a white solid which was collected by filtration and dried at 60° C. in vacuo (1.01 g, 5.82 mmol, 29%); δH [$^2$H$_6$]DMSO 9.27 (2H,br s), 3.59 (2H,dd), 3.31 (2H,dd), 2.57 (3H,s).

N-[2-(Methanesulphonamido)ethyl]acetamide

N-Acetylethylenediamine (10.2 g, 100 mmol) and triethylamine (15 ml, 10.9 g, 108 mmol) were dissolved in dichloromethane (300 ml) and the solution cooled to 0° C. Methanesulphonyl chloride (8 ml, 11.8 g, 103 mmol) was dissolved in dichloromethane (10 ml) and added dropwise, and stirring was continued at 0° C. for 3 hours. The dichloromethane was removed in vacuo, and the residue was suspended in a mixture of ether and acetone, removing the insoluble material by filtration. The filtrate was concentrated in vacuo to give the title compound as a pale brown gum (14.5 g, 88.3 mmol, 88%); δH [$^2$H$_6$]DMSO 7.93 (1H,br t), 7.05 (1H,t), 3.11 (2H,t), 2.97 (2H,t), 2.89 (3H,s), 2.09 (3H,s).

2-(Methanesulphonamido)ethylamine hydrochloride

N-[2-(Methanesulphonamido)ethylgacetamide (14.5 g, 88.3 mmol) and concentrated hydrochloric acid (100 ml) were dissolved in water (100 ml) and heated to reflux for a total of 3 hours. After cooling, the water was removed in vacuo, and the residue was left for several days at room temperature until crystallisation was underway.

Trituration with a mixture of ethanol and ether gave the title compound as a white solid which was dried in vacuo at 60° C. (7.5 g, 42.9 mmol, 49%); δH [$^2$H$_6$]DMSO 8.22 (2H,br s), 7.42 (1 H,t), 3.23 (2H,q), 2.87 (3H,s), 2.85–2.95 (2H,m).

The following preparations, although not resulting in compounds of the present invention, illustrate the synthetic procedures used to prepare compounds bearing a substituted 1,3,4-oxadiazole ring; analogous procedures would be used to prepare compounds of the present invention.

6-Cyano-pyrido[3,4-pyrimidin-4-one

6-Chloro pyrido[3,4-d]pyrimidin-4-one (10 g) in 1-methyl-2-pyrrolidinone (100 ml) was treated with copper (I) iodide (10.52 g) and potassium cyanide (7.10 g) at 215° C. for 72 hours under N$_2$. Further potassium cyanide was added (3.58 g) and heating continued at 230° C. for 70 hours. The 1-methyl-2-pyrrolidinone was removed by distillation at reduced pressure and the residue absorbed onto silica. Chromatography gave the title compound (2.4 g) as a beige solid; δH [$^2$H$_6$]DMSO 13.0 (1H,bs), 9.25 (1H,s), 8.55 (1H,s), 8.50 (1H,s); m/z (M–1$^+$) 171.

6-(1,2,3,4-Tetrazol-5-yl_-pyrido[3,4-d]pyrimidin-4-one

6-Cyano-pyrido[3,4-d]pyrimidin4-one (0.3 g) in diglyme (2 ml) was treated with tributyl tin azide (0.49 g) at reflux under N$_2$ for 15 hours. The cooled mixture was partitioned between ethyl acetate and water and the aqueous phase extracted further with ethyl acetate. The aqueous phase was concentrated in vacuo, the residue taken up in methanol and inorganics removed by filtration. Subsequent concentration gave the title compound (1.4 g) as a beige solid; δH [$^2$H$_6$]DMSO 8.96 (1H,s), 8.50 (1H,s), 8.27 (I H,s); m/z (M+1$^+$) 216.

6-(5-Methyl-1,3,4-oxadiazol-2-yl)pyrido]3,4-d [pyrimidin-4-one 6-(1,2,3,4-Tetrazol-5-yl) pyrido[3,4-d]pyrimidin-4-one (1.4 g) in acetic anhydride (10 ml) was heated at reflux under N$_2$ for 2.5 hours. The cooled mixture was absorbed onto silica and purified by chromatography to give the title compound (0.14 g) as a beige solid; δH [$^2$H$_6$]DMSO 13.0 (1H,bs), 9.30 (1H,s), 8.66 (1H,s), 8.47 (1H,s) 2.75 (3H,s); m/z (M+1$^+$) 230.

4-Chloro-6-(5methyl-1,3,4-oxadiazol-2-yl)pyrido[3,4-d] pyrimidine 6-(5-Methyl-1,3,4-oxadiazol-2-yl)-pyrido[3,4-d] pyrimidin-4-one (0.5 g) was treated with phosphorus oxychloride in the usual manner to give the title compound (0.17 g) as an orange solid; δH CDCl₃ 9.68 (1H,s), 9.30 (1H,s), 8.96 (1H,s), 2.75 (3H,s); m/z (M+1⁺) 248.

(4-Phenoxy-phenyl)-6-(5-methyl-1,3,4-oxadiazol-2-yl)-pyrido3,4-d]pyrimidin-4-yl)-amine The title compound was prepared according to Procedure A from 4-phenoxyaniline and 4-chloro-6-(5-methyl-1,3,4-oxadiazol-2-yl)-pyrido[3,4-d]pyrimidine; δH [²H]DMSO 11.15 (1H,s), 9.43 (1H,s), 9.34 (1H,s), 8.89 (1H,s), 7.86 (2H,d), 7.45 (2H,dd), 7.12 (5H,m), 2.75 (3H,s); m/z (M+1⁺) 397.

(4-(3-Fluoro-benzyloxyhphenyl)-(6-(5-methyl-1,3,4-oxadiazol-2-yl)-pyrido[3,4-d]pyrimidin-4-yl)-amine The title compound was prepared according to Procedure A from 4-(3-Fluoro benzyloxy)aniline and 4-chloro-6-(5-methyl-1,3,4-oxadiazol-2-yl)-pyrido[3,4-d]pyrimidine; δH [²H₆]DMSO 11.30 (1H,s), 9.47 (1H,s), 9.38 (1H,s), 8.93 (1H,s), 7.80 (2H,d), 7.53 (1H,m), 7.38 (2H,d), 7.22 (3H,m), 5.25 (2H,s), 2.74 (3H,s); m/z (M+1⁺) 429.

(4-Benzyloxy-phenyl)-(6-(5-methyl-1,3,4-oxadiazol-2-yl)-pyrido[3,4-d]pyrimidin-4yl)-amine The title compound was prepared according to Procedure A from 4-benzyloxyaniline and 4-chloro-6-(5-methyl-1,3,4-oxadiazol-2-yl)pyrido[3,4-d]pyrimidine; δH [²H₆]DMSO 11.33 (1H,s), 9.49 (1H,s), 9.39 (1H,s), 8.93 (1H,s), 7.80 (2H,d), 7.53 (2H,dd), 7.45 (3H,m), 7.20 (2H,d), 5.25 (2H,s), 2.75 (3H,s); m/z (M+1⁺) 411.

(4-Benzenesulphonyl-phenyl)-(6-(5-methyl-1,3,4-oxadiazol-2-yl-pyrido[3,4-d]pyrimidin-4-yl)-amine The title compound was prepared according to Procedure A from 4-benzenesulphonylaniline and 4-chloro-6-(5-methyl-1,3,4-oxadiazol-2-yl)-pyrido[3,4-d]pyrimidine; m/z (M+1⁺) 411.

EXAMPLES

Example 1

(4-Benzyloxy-phenyl)-(6-(5-piperidin-1-ylmethyl)-furan-2-yl)-pyrido3,4-d]pyrimidin-4-yl)-amine hydrochloride 5-(4-(4-Benzyloxy-phenylamino)pyrido[3,4-d]pyrimidin-6-yl)-furan-2-carbaldehyde (0.2 g) and piperidine (0.2 g) were mixed in dichloromethane (2ml) and stirred at room temperature for 5 minutes. The mixture was chilled to 0° C. and sodium triacetoxyborohydride (0.5 g) added in portions with stirring. The reaction was stirred at 0° C. for 15 minutes and then at room temperature for 1 hour. The reaction was quenched with water and diluted with dichloromethane. The organic phase was separated and the aqueous extracted with dichloromethane. The combined organic fractions were dried (MgSO₄) and the solvent removed under vacuum. The resulting yellow glass was dissolved in acetone, filtered and the filtrate acidified with 2N HCl. The solid produced was filtered off, washed with acetone and dried at 60° C. under vacuum to give the product as a yellow solid (0.192 g); δH [²H₆]-DMSO 11.90 (1H, bs), 10.79 (1H, bs), 9.70 (1H, s), 9.34 (1H, s), 8.92 (1H, s), 7.91 (2H, d), 7.60–7.40 (6H, m), 7.20 (2H, d), 7.02 (1H, d), 5.23 (2H, s), 4.58 (2H), 3.50 (2H, d), 3.04 (2H, b), 2.02–1.70 (5H, m), 1.47 (1H, m); m/z 492 (M+1)⁺.

Example 2

(4-Benzyloxy-phenyl)-(6-(5-(4-methyl-piperazin-1-ylmethy)-furan-2-yl)pyrido[3,4-d]pyrimidin-4-yl)-amine In an analogous manner to Example 1, 5-(4-(4-Benzyloxy-phenylaminoypyrido[3,4-d]pyrimidin-6-yl)-furan-2-carbaldehyde and 1-methylpiperazine were converted into the title compound; δH [²H₆]-DMSO 10.29 (1H, b), 9.11 (1H, s), 8.66 (1H, s), 8.60 (1H, s), 7.72 (2H, d), 7.52–7.33 (5H, m), 7.15–7.06 (3H, m), 6.55 (1H, d), 5.15 (2H, s), 3.62 (2H, s), 2.61–2.28 (δH, m), 2.15 (3H, s); m/z 507 (M+1)⁺.

Example 3

4-Benzyloxy-phenyl)-(6-(5-((2-methanesulphonyl-ethylamino)methyl)-furan-2-yl-pyrido[3,4-d]pyrimidin-4-yl)-amine hydrochloride In an analogous manner to Example 1, 5-(4-(4-Benzyloxy-phenylamino)-pyrido[3,4-d]pyrimidin-6-yl)-furan-2-carbaldehyde and 2-(methanesulphonylyethylamine were converted into the title compound; δH [²H₆] DMSO 11.73 (1H, b), 10.00 (1H, b), 9.62 (1H, s), 9.21 (1H, s), 8.81 (1H, s), 7.80 (2H, d), 7.49–7.24 (6H, m), 7.09 (2H, d), 6.84 (1H, d), 5.11 (2H, s), 4.41 (2H, s), 3.69 (2H, t), 3.53 (2H, b).; m/z 530 (M+1)⁺.

Example 4

((5-4-(4-Benzloxy-phenylamino)-pyrido[3,4-d]pyrimidin-6-yl)-furan-2-ylmethyl)-amino)-acetic acid methyl ester hydrochloride In an analogous manner to Example 1, 5-(4-(4-Benzyloxy-phenylaminoypyrido[3,4-d]pyrimidin-6-yl)-furan-2-carbaldehyde and glycine methyl ester hydrochloride were converted into the title compound; δH [²H₆]-DMSO 9.26 (1H, s), 9.19 (1H, s), 8.77 (1H, s), 7.90 (2H, d), 7.64–7.42 (5H, m), 7.36 (1H, d), 7.20 (2H, d), 6.98 (1H, d), 5.25 (2H, s), 4.51 (2H, s), 4.20 (2H, s), 3.86 (3H, s); m/z 496 (M+1)⁺.

Example 5

(4-Benzyloxy-phenyl)-(6-(5-(pyridin-3-ylaminomethyl)-furan-2-yl)-pyrido[3,4-d]pyrimidin-4-yl)-amine In an analogous manner to Example 1, 5-(4-(4-Benzyloxy-phenylamino)-pyrido[3,4-d]pyrimidin-6-yl)-furan-2-carbaldehyde and 3-aminopyridine were converted into the title compound; δH [²H₆]-DMSO 10.42 (1H, b), 9.08 (1H, s), 8.69 (1H, s), 8.55 (1H, s), 8.09 (1H, d), 7.79 (1H, d), 7.70 (2H, d), 7.52–7.27 (5H, m), 7.16–6.99 (5H, m), 6.52 (2H, m), 5.11 (2H, s), 4.42 (2H, d); m/z 501 (M+1)⁺.

Example 6

(4-Benzyloxy-phenyl)6-(5-(dimethyyaminomethyl)-furan-2-yl)pyrido[3,4-d]pyrimidin4-yl)-amine hydrochloride In an analogous manner to Example 1, 5-(4-(4-Benzyloxy-phenylamino)-pyrido[3,4-d]pyrimidin-6-yl)-furan-2-carbaldehyde and dimethylamine hydrochloride were converted into the title compound; δH [²H₆]-DMSO 9.50 (1H, s), 9.26 (1H, s), 8.84 (1H, s), 7.87 (2H, d), 7.57–7.32 (6H, m), 7.17 (2H, d), 6.99 (1H, d), 5.20 (2H, s), 4.57 (2H, s), 2.88 (6H, s); m/z 452 (M+1)⁺.

Example 7

(2S)-1-(5-(4-(4-Benzyloxy-phenylamino)-pyrido[3,4-d]pyrimidine-6-yl)-furan-2-ylmethyl)-pyrrolidine-2-carboxylic acid amide hydrochloride In an analogous manner to Example 1, 5-(4-(4-Benzyloxy-phenylamino)-pyrido[3,4-d]pyrimidin-6-yl)-furan-2-carbaldehyde and L-prolinamide were converted into the title compound; δH [²H₆]-DMSO 9.92 (1H, b), 9.52 (1H, s), 9.28 (1H, s), 8.83 (1H, s), 8.49 (1H, s), 7.81 (2H, d), 7.71 (1H, s), 7.58–7.28 (6H, m), 7.14 (2H, d), 6.91 (1H, d), 5.19 (2H, s), 4.80 (1H, b), 4.60 (2H, s), 3.67 (1H, b), 3.40 (1H, b), 2.17–1.74 (4H, m); m/z 521 (M+1)+.

Example 8

2-((5-(4-(4-Benzyloxy-phenylamino)-pyrido[3,4-d]pyrimidin-6-yl)-furan-2-ylmethyl)-methylamino)-acetamide In an analogous manner to Example 1, 5-(4-(4-Benzyloxy-phenylamino)pyrido[3,4-d]pyrimidin-6-yl)-furan-2-carbaldehyde and sarcosinamide were converted into the title compound; δH [$^2$H$_6$] DMSO 10.21 (1H, b), 9.11 (1H, s), 8.65 (1H, s), 8.60 (1H, s), 7.72 (2H, d), 7.54–7.33 (5H, m), 7.28, (1H, b), 7.18, (1H, b), 7.15–7.05 (3H, m), 6.51 (1H, d), 5.15 (2H, s), 3.79 (2H, s), 3.02 (2H, s), 2.32 (3H, s); m/z 495 (M+1)+.

Example 9

N-(2-((5-(4-(4Benzyloxy-phenylamino)-pyrimido[3,4-d]pyrimidin-6-yl)-furan-2-ylmethyl)-amino)-ethyl)-acetamide In an analogous manner to Example 1, 5-(4-(4-Benzyloxy-phenylamino)-pyrido[3,4-d]pyrimidin-6-yl)-furan-2-carbaldehyde and N-acetylethylenediamine were converted into the title compound; δH [1$^2$H$_6$]-DMSO 10.25 (1H, b), 9.10 (1H, s), 8.65 (1H, s), 8.59 (1H, s), 7.86, (1H, b), 7.72 (2H, d), 7.52–7.31 (5H, m), 7.15–7.05 (3H, m), 6.50 (1H, d), 5.14 (2H, s), 3.83 (2H, s), 3.18 (2H, q), 2.64 (2H, t), 2.20 (1H, bs), 1.79 (3H, s); m/z 509 (M+1)+.

Example 10

(4-Benzyloxy-phenyl)-(6-(5-((2-methanesulphinyl-ethylamino)-methyl)-furan-2-yl)-pyrido[3,4-d]pyrimidin-4-yl)-amine In an analogous manner to Example 1, 5-(4-(4-Benzyloxy-phenylamino)-pyrido[3,4-d]pyrimidin-6-yl)-furan-2-carbaldehyde and [2-(methanesulphinyl)ethyl]amine were converted into the title compound; δH [$^2$H$_6$]-DMSO 10.20 (1H, b), 9.11 (1H, s), 8.67 (1H, s), 8.59 (1H, s), 7.72 (2H, d), 7.53–7.30 (5H, m), 7.17–7.04 (3H, m), 6.52 (1H, d), 5.15 (2H, s), 3.87 (2H, s), 3.08–2.75 (4H, m), 2.55 (3H, s); m/z 514 (M+1)+.

Example 11

((5-(4-(4-Benzyloxy-phenylamino)-pyrido[3,4-d]pyrimidine-6yl)-furan-2-ylmethyl)-amino)-acetic acid hydrochloride ((5-(4-(4-Benzyloxy-phenylamino)-pyrido[3,4-d]pyrimidin-6-yl)-furan-2-ylmethyl)-amino)acetic acid methyl ester hydrochloride (0.04 g) was suspended in acetone (5 ml) and 2N sodium hydroxide solution (5 ml) added. The resulting solution was stirred at room temperature for 30 mins. The acetone was removed under vacuum and the solution acidified with 2N HCl. The mixture was chilled in an ice-bath and the precipitate filtered off and washed with a little cold water and then acetone. The residue was dried at 60° C. under vacuum to give the product as an orange solid (0.03 g); δH [$^2$H$_6$]-DMSO 10.30 (1H, b), 9.10 (1H, s), 8.71 (11H, s), 8.59 (11H, s), 7.75 (2H, d), 7.53–7.28 (5H, m), 7.15–7.00 (3H, m), 6.62 (1H, d), 5.12 (2H, s), 4.07 (2H, s); m/z 482 (M+1)+.

Example 12

(5-4-(4-(4-Benzyloxy-phenylamino)-pyrido[3,4-d]pyrimidin-6-yl)-furan-2-yl)-methanol hydrochloride 5-(4-(4-Benzyloxy-phenylamino)-pyrido[3,4-d]pyrimidin-6-yl)-furan-2carbaldehyde (0.2 g) was suspended in methanol (5 ml) and sodium borohydride (0.026 g) added. The reaction was stirred at room temperature for 1 hour then acidified with 2N HCl. The methanol was removed under vacuum, the residue diluted with acetone and the resulting orange solid filtered off and washed with water and acetone. The solid was suspended in 1:1 ethyl acetate/iso-hexane and neutralised with triethylamine, the solution formed was columned on a silica gel flash column eluting with an ethyl acetate/iso-hexane gradient (50–100% ethyl acetate) and finally with acetone. The product fractions were concentrated under vacuum and the resulting oil was dissolved in acetone and acidified with ethereal HCl (1 N) which after drying at 60° C. under vacuum gave the product as an orange solid (0.8 g, ); δH [$^2$H$_6$]-DMSO 11.80 (1H, b), 9.30 (11H, s), 9.05 (1H, s), 8.90 (1H, s), 7.79 (2H, d), 7.60–7.38 (5H, m), 7.31 (1H, d), 7.21 (2H, d), 6.65 (1H, d), 5.23 (2H, s), 4.63 (2H, s); m/z 425 (M+1)+. On another occasion purification of the oil by column chromatography, eluting with 3–10%MeOH/CHCl$_3$, gave the free base of the product as a yellow solid; δH C$^2$H,DMSO 10.33 (1H,s), 9.74 (1H,s) 8.68 (1H,s), 8.60 (1H,s), 7.71 (2H,d), 7.337.51 (5H,m), 7.05–7.13 (3H,m), 6.54 (1H,d), 5.14 (2H,s).

Example 13

(2R)-1-{5-[4-(4-Benzyloxy-phenylamino)-pyrido[3,4-d]pyrimidin-6-yl]-furan-2-ylmethyl}pyrrolidine-2-carboxalic acid amide hydrochloride In an analogous manner to Example 7, 5-(4-(4-Benzyloxy-phenylamino)pyrido[3,4-d]pyrimidin-6-yl)-furan-2-carbaldehyde (0.200 g, 0.47 mmol) was reacted with D-prolinamide (0.270 g, 2.37 mmol). Purification by silica gel chromatography, eluting with 3–5% MeOH/CHCl$_3$, gave an orange oil. This was treated with ethereal HCl, followed by trituration with ethyl acetate/ihexane, to give the product as an orange solid which was dried at 60° C. in vacuo (0.150 g, 0.253 mmol, 54%); 5H [$^2$H$_6$]DMSO 12.35 (1H,s), 9.51 (1H,s), 9.27 (1H,s), 8.86 (1H,s), 8.45 (1H,s), 7.80 (2H,d), 7.70 (1H,s), 7.30–7.52 (6H,m), 7.13 (2H,d), 6.92 (1H,d), 5.17 (2H,s), 4.42 (1H,t), 3.30, 3.50 (2H,m, obscured by water), 1.80–2.10 (4H,m); m/z (M+1+) 521.

Example 14

(4-Benzyloxy-phenyl)-6-(5-((3-methanesulphonyl-propylamino)methyl)-furan-2-yl)-pyrido[3,4-d]pyrimidin-4-yl)-amine In an analogous manner to Example 1, 5 (4-(4-Benzyloxy-phenylamino)-pyrido[3,4-d]pyrimidin-6-yl)-furan-2-carbaldehyde and 3-methanesulphonyl-propylamine were converted into the title compound; δH [$^2$H$_6$]-DMSO 10.35 (1H,s), 9.23 (1H,s), 9.02 (1H,s), 8.72 (1H,s), 7.90 (2H,d), 7.63–7.40 (5H,m), 7.27 (1H,d), 7.20 (2H,d), 6.80 (1H,d), 5.25 (2H,s), 4.22 (2H,s), 3,40 (2H,m), 3.09 (3H,s), 3.04 (2H,m), 2.12 (2H,m); m/z (M+1)+544.

Example 15

(4-Benzyloxy-phenyl)-(6-(5-(((2-methanesulphonyl-ethyl)-methyl-aminomethyl)-furan-2-yl)-pyrido[3,4-d]pyrimidin-4-yl)-amine In an analogous manner to Example 1, 5-(4-(4-Benzyloxy-phenylamino)-pyrido[3,4-d]pyrimidin-6-yl)-furan-2-carbaldehyde (0.217 g, 0.473 mmol) was reacted with N-methyl-N-(2-methanesulphonylethyl)-amine (0.411 g, 3.00 mmol). Purification by silica gel chromatography, eluting with 2–5% MeOH/CHCl$_3$, followed by trituration with ether gave the product as a pale yellow solid (0.0309, 0.055 mmol, 12%); δH [²H₆]DMSO 10.20 (1H,s), 9.11 (1H,s), 8.63 (1H,s), 8.59 (1H,s), 7.71 (2H,d), 7.33–7.52 (5H,m), 7.06–7.14 (3H,m), 6.59 (1H,d), 5.14 (2H,s), 3.72 (2H,s), 3.20–3.40 (2H,m, obscured by water), 3.04 (3H,s), 2.85 (2H,t), 2.29 (3H,s); m/z (M+1⁺) 544.

Example 16

(2S)-1-{-5-[4-(4-Benzyloxy-phenylamino)-pyrido[3,4-d]pyrimidin-6-yl]-furan-2-ylmethyl}-pyrrolidine-2-carboxylic acid dimethylamide In an analogous manner to Example 7, 5-(4-(4-Benzyloxy-phenylamino)pyrido[3,4-d]pyrimidin-6-yl)-furan-2-carbaldehyde (0.217 g, 0.472 mmol) was reacted with L-N,N-dimethylprolinamide (0.2409, 2.10 mmol). Purification by silica gel chromatography, eluting with 2–4% MeOH/CHCl₃, followed by concentration from ether/i-hexane gave the product as a pale yellow solid (0.127 g, 0.231 mmol, 49%); δH [²H₆]DMSO 10.25 (1H,s), 9.10 (1H,s), 8.62 (1H,s), 8.58 (1H,s), 7.71 (2H,d), 7.32–7.52 (5H,m), 7.057.12 (3H,m), 6.46 (1H,d), 5.14 (2H,s), 3.83 (2H,quart), 3.51–3.63 (1H,m), 3.32 (2H,m, obscured by water), 2.96 (3H,s), 2.77 (3H,s), 1.63–1.82 (4H,m); m/z (M+1⁺) 549.

Example 17

N-(2-((5-(4-(4-Benzyloxy-phenylamino)-pyrido[3,4-d]pyrimidin-6-yl)-furan-2-ylmethyl)-amino)-ethyl)-methanesulphonamide hydrochloride In an analogous manner to Example 1, 5-(4-(4-Benzyloxy-phenylamino)-pyrido[3,4-d]pyrimidin-6-yl)-furan-2-carbaldehyde (0.200 g, 0.435 mmol) was reacted with 2-(methanesulphonamido)ethylamine (0.350 g, 2.53 mmol) and triethylamine (10 drops). Quenching of the reaction mixture with water, acidification to pH1 with dilute HCl, and dilution with acetone gave a yellow precipitate. This was collected by filtration, and washed with water and acetone to give the product as a yellow solid which was dried at 60° C. in vacuo (0.200 g, 0.324 mmol, 74%); δH [²H₆]DMSO 11.40 (1H,s), 9.63 (2H,br s), 9.50 (1H,s), 9.22 (1H,s), 8.82 (1H,s), 7.85 (2H,d), 7.12–7.32 (5H,m), 7.11 (1H,d), 7.13 (2H,d), 6.88 (1H,d), 5.17 (2H,s), 4.42 (2H,s), 3.35–3.43 (2H,m), 3.13–3.21 (2H,m), 2.98 (3H,s); m/z (M+1⁺) 545.

Example 18

(4-Benzyloxyphenyl)-(6-(5-(1,3-dioxolan-2-yl-furan-2-yl)-pyrido[3,4-d]pyrimidin-4-yl)-amine Reaction of (4-benzyloxyphenyl)-(6-chloro-pyrido[3,4-d]pyrimidin-4-yl)-amine (5.44 g, 15.0 mmol), 5-(1,3-dioxolan-2-yl)-2-(tributylstannyl)-furan (10.4 g, 24.2 mmol) and bis-(triphenylphosphine)palladium (II) chloride (catalytic amount) in dioxane (150 ml) according to Procedure B, followed by purification by silica gel chromatography (eluted with 50–100% EtOAc/i-hexane), allowed the isolation of the dioxolane product (3.45 g, 7.40 mmol, 49%); δH [²H₆]DMSO 10.28 (1H,s), 9.13 (1H,s), 8.69 (1H,s), 8.61 (1H,s), 7.71 (2H,d), 7.31–7.52 (5H,m), 7.14 (1H,d), 7.09 (2H,d), 6.77 (1H,d), 6.03 (1H,s), 5.15 (2H,s), 3.95–4.19 (4H,m).

Examples 19 to 24

The following compounds and their hydrochloride salts, if appropriate, are prepared by analogous techniques using the appropriate starting materials:

(4-Benzyloxy-phenyl)-(6-(5-(4-methyl-piperazin-1-ylmethyl)-N-methylimidazol-2-yl-pyrido[3,4-d]pyrimidin4-yl)-amine;

(4-Benzyloxy-phenyl)-(6-(5-(dimethylaminomethyl)-N-methylimidazol-2-yl)-pyrido[3,4-d]pyrimidin4-yl)-amine;

(4-Benzyloxy-phenyl)-(6-(5-(4-methyl-piperazin-1-ylmethylyimidazol-2-yl)-pyrido[3,4-d]pyrimidin4-yl)-amine;

(4-Benzyloxy-phenyl-(6-(5-(dimethylaminomethylyimidazol-2-yl)-pyrido[3,4-d]pyrimidin-4-yl)-amine;

(4-Benzyloxy-phenyl)-(6-(1-(4-methyl-piperazin-1-ylmethyl)-N-methylimidazol-2-yl)pyrido[3,4-d]pyrimidin4-yl)-amine;

(4-Benzyloxy-phenyl)-(6-(1-(dimethylaminomethyl)-N-methylimidazol-2-ylypyrido[3,4-d]pyrimidin4-yl)-amine.

Biological Data

Compounds of the present invention were tested for protein tyrosine kinase inhibitory activity in substrate phosphorylation assays and cell proliferation assays.

The substrate phosphorylation assays use baculovirus expressed, recombinant constructs of the intracellular domains of c-erbB-2 and c-erbB4 that are constitutively active and EGFr isolated from solubilised A431 cell membranes. The method measures the ability of the isolated enzymes to catalyse the transfer of the γ-phosphate from ATP onto tyrosine residues in a biotinylated synthetic peptide (Biotin-GluGluGluGluTyrPheGluLeuVal). The enzyme is incubated for 30 minutes, at room temperature, with 10 mM McCl₂, ATP and peptide at Km concentrations, and test compound (diluted from a 5 mM stock in DMSO, final DMSO concentration is 2%) in 40 mM HEPES buffer, pH 7.4. The reaction is stopped by the addition of EDTA (final concentration 0.15 mM) and a sample is transferred to a streptavidin-coated 96-well plate. The plate is washed and the level of phosphotyrosine on the peptide is determined using a Europium-labelled antiphosphotyrosine antibody and quantified with a time-resolved fluorescence technique. The results are shown in Table 1 as the IC₅₀ values in nM.

The cell proliferation assay uses an immortalised human breast epithelial cell line (HB4a) which has been transformed by over-expression of c-erbB-2. Growth of these cells in low serum is dependent upon the c-erbB-2 tyrosine kinase activity. The specificity of the effect of the test compounds on tyrosine kinase dependent growth over general toxicity is assessed by comparison to an HB4a cell line which has been transfected with ras. Cells are plated at 3000/well in 96-well plates in 0.1 t-5 ml medium and allowed to attach overnight. test compound is added in 0.1 ml medium, with a final concentration of 0.5% DMSO, and the plates incubated for 4 days at 37° C. The cells are then examined microscopically for evidence of morphological detransformation and cell mass is estimated by staining with methylene blue and measuring the absorbance at 620 nm. The results are shown in Table 1 below as the IC50 values in nM. Activity against a range of naturally occurring EGFr or c-erbB-2 over-expressing human tumour cell lines (BT474-breast, HN5-head and neck, N87 gastric and Calu3-lung) is assessed with selected compounds by the same methodology. The results are also shown in Table 1 below as the IC50 values in nM.

TABLE 1

| | Substrate Phosphorylation | | | Cell Proliferation | | | | | |
|---|---|---|---|---|---|---|---|---|---|
| Example | EGFr | erbB-2 | erbB-4 | HB4a erbB-2 | HB4a ras | BT474 | N87 | Calu3 | HN5 |
| 1 | 170 | 70 | 1400 | | | | | | |
| 2 | 170 | 60 | 760 | 430 | 2100 | | | | |
| 3 | 140 | 10 | 190 | 500 | 31000 | | | | |
| 4 | 130 | 13 | 530 | 29000 | 16000 | | | | |
| 5 | 260 | 110 | 1600 | 5600 | 8200 | | | | |
| 6 | 380 | 98 | 2400 | 1500 | 2200 | | | | |
| 7 | 79 | 44 | 84 | 410 | 15000 | | | | |
| 8 | 720 | 11 | 160 | 100 | 41000 | 380 | 60 | 340 | 350 |
| 9 | 95 | 7 | 1000 | 730 | 3900 | | | | |
| 10 | 140 | 22 | | 250 | 8700 | | | | |
| 11 | 88 | 19 | 450 | 50000 | 5900 | | | | |
| 12 | 31 | 4 | 490 | 440 | 7600 | | | | 460 |
| 13 | | 14 | 480 | 170 | >50000 | | | | 350 |
| 14 | | 420 | 3900 | | | | | | |
| 15 | | 30 | 1500 | 300 | 8500 | | | | |
| 16 | | 280 | 2800 | 2100 | 7900 | | 670 | | 3300 |
| 17 | | 29 | 760 | 250 | 3500 | 100 | 150 | 3700 | 720 |

What is claimed is:
1. A compound of formula (I):

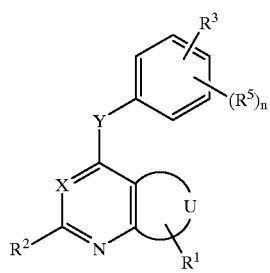

or a salt or solvent thereof;
wherein X is N;
  Y is a group W(CH$_2$), (CH$_2$)W, or W, in which W is O, S(O)$_m$ wherein m is 0, 1 or 2, or NR$^a$ wherein R$^a$ is hydrogen or a C$_{1-8}$ alkyl group;
  R$^1$ is selected from the group consisting a phenyl, furan, thiophene, pyridine, pyrimidine, pyrazine, pyrrole, oxazole, isoxazole, oxadiazole, thiazole, isothiazole, triazole, tetrazole and imidazole ring or a hydrogenated derivative of the aforementioned, the ring being substituted:
  either (a) by one or more groups selected from dioxolanyl, hydroxy- C$_{1-4}$ alkyl C$_{1-4}$ alkylamino-C$_{1-4}$ alkyl or di(C$_{1-4}$ alkyl)-amino- C$_{1-4}$ alkyl;
  or (b) by one or more groups independently selected from M$^1$-M$^2$-M$^3$-M$^4$, M$^1$-M$^5$ or M$^1$-M$^2$-M$^3$'-M$^6$
wherein
  M$^1$ represents a C$_{1-4}$ alkyl group, wherein optionally a CH$_2$ group is replaced by a CO group;
  M$^2$ represents NR$^{12}$ or CR$^{12}$ and R$^{13}$ each independently represent H or C$_{1-4}$ alkyl;
  M$^3$ represents a C$_{1-4}$ alkyl group;
  M$^3$ represents a C$_{1-4}$ alkyl group or is absent;
  M$^4$ represents CN, NR$^{12}$S(O)$_m$R$^{13}$, S(O)$_m$NR$^{14}$R$^1$, CONR$^{14}$R$^{15}$, S(O)$_m$R$^{13}$ or CO$_2$R$^{13}$, in which R$^{12}$, R$^{13}$ and m are as hereinbefore defined and R$^{14}$ and R$^{15}$ each independently represent H or C$_{1-4}$ alkyl, or R$^{14}$ and R$^{15}$ together with the nitrogen atom to which they are attached represent a 5-or 6-membered ring optionally containing 1 or 2 additional heteroatoms selected from N, O or S(O)$_m$ in which ring any nitrogen atom present may optionally be substituted with a C$_{1-4}$ alkyl group;
  M$^5$ represents the group NR$^{14}$R$^{15}$ or the group

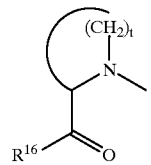

in which t represents 2 to 4 and R$^{16}$ represents OH, OC$_{1-4}$ alkyl or NR$^{14}$R$^{15}$; and
  M$^6$ represents a C$_{3-6}$ cycloalkyl group, the group NR$^{14}$R$^{15}$ or a 5- or 6membered heterocyclic ring system containing 1 to 4 heteroatoms selected from N, O or S;
  and R$^1$ is optionally further substituted by one or two halogeno, C$_{1-4}$ alkyl or C$_{1-4}$ alkoxy groups;
  R$^2$ represents hydrogen;
  each R$^5$ is independently selected from the group consisting hydrogen, hydroxy, halogen, C$_{1-4}$ alkyl, C$_{1-4}$ alkoxy, C$_{1-4}$ alkylamino, di-[C$_{1-4}$ alkylamino, C$_{1-4}$ alkylthio, C$_{1-4}$ alkylsulphinyl, C$_{1-4}$ alkylsulphonyl, C$_{1-4}$ alkylcarbamoyl, di-carbamoyl, carbamyl, C$_{1-4}$ alkoxycarbonyl, cyano, nitro and trifluoromethyl, and n is 1, 2 or 3;
  R$^3$ is a group ZR$^4$ wherein Z is joined to R$^4$through a (CH$_2$)p group in which p is 0, 1 or 2 and Z is oxygen, dicarbonyl, OCH$_2$, CH(CN), S(O)$_m$ or NR$^b$, wherein R$^b$ is hydrogen or C$_{1-4}$ alkyl; and R$^4$ is an optionally substituted phenyl, dioxolanyl, thienyl, cyclohexyl or pyridyl group;
wherein any optional substituent on R$^4$ is either (a) selected from the group consisting CH$_2$)$_q$S(O)$_m$C$_{1-4}$ alkyl, (CH$_2$)$_q$S(O)$_m$-C$_{3-6}$ cycloalkyl, (CH$_2$)$_q$SO$_2$NR$^8$R$^9$, (CH$_2$)$_q$CO$_2$R$^8$, (CH$_2$)$_q$OR$^8$, (CH$_2$)$_q$CONR$^8$R$^9$, (CH$_2$)$_q$NR$^8$COR$^9$, (CH$_2$)$_q$COR$^8$, (CH$_2$)$_q$R$^8$, NRSSO$_2$R$^9$ and S(O)$_m$R$^8$; wherein q is an integer from 0 to 4 inclusive and m is as defined above;

and wherein $R^8$ and $R^9$ are independently selected from the group consisting hydrogen, Ci- alkyl, $C_{3-5}$ cycloalkyl, aryl, a 5-or 6-membered saturated or unsaturated heterocyclic ring which may be the same or different and which contains one or more heteroatoms which are selected from N, O or $S(O)_m$, with the proviso that the heterocyclic ring does not contain two adjacent O or $S(O)_m$ atoms; or (b) is selected from the group consisting halogen, trifluoromethyl, trifluoromethoxy, nitro and cyano;

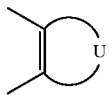

and
represents

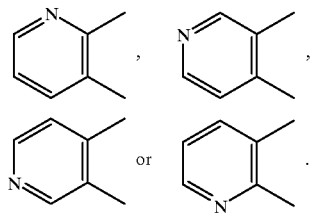

2. A compound as claimed in claim 1 wherein Y is $NR^a$, $NR^a(CH_2)$, or $(CH_2)NR^a$.

3. The compound of claim 2, wherein Y is N $R^a$ and $R^a$ is hydrogen and methyl.

4. A compound as claimed in claim 1 wherein $R^1$ is as defined in claim 1 substituted with a group selected from $M^1$-$M^2$-$M^3$-$M^4$, $M^1$-$M^5$ or $M^1$-$M^2$-$M^{3'}$-$M^6$ as defined in claim 1.

5. A compound as claimed in claim 1 wherein $M^1$ represents $CH_2$, CO, $CH_2CH_2$ or $CH_2CO$; $M^2$ represents $NR^{12}$ in which $R^{12}$ is as defined in claim 1; $M^3$ represents $CH_2$, $CH_2CH_2$ or propyl; $M^{3'}$ represents $CH_2$, ethyl, propyl, isopropyl or is absent; $M^4$ represents $SOR^{13}$, $SO_2R^{13}$, $NR^{12}SO_2R^{13}$, $CO_2R^{13}$ or $CONR^{14}R^{15}$ in which $R^{12}$ and $R^{13}$ are defined in claim 1 and $R^{14}$ and $R^{15}$ each independently represent H or $C_{1-4}$ alkyl; $M^5$ represents a group $NR^{14}R^{15}$ in which $R^{14}$ and $R^{15}$ together with the nitrogen atom to which they are attached represent a 6-membered ring optionally containing an additional heteroatom selected from N or O, in which ring any nitrogen atom present may optionally be substituted with a $C_{1-4}$ alkyl group; or $M^5$ represents a group

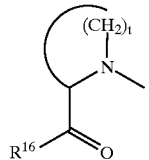

in which t represents 2 or 3 and $R^{16}$ represents OH, $NH_2$, $N(C_{1-4}$ alkyl$)_2$ or $OC_{1-4}$ alkyl; or $M^5$ represents a group $NR^{14}R^{15}$ in which $R^{14}$ and $R^{15}$ each independently represent hydrogen or $Ca_{1-4}$ alkyl $M^6$ represents a group $NR^{14}R^{15}$ in which $R^{14}$ and $R^{15}$ each independently represent $C_{1-4}$ alkyl, more preferably methyl, or $R^{14}$ and $R^5$ together with the nitrogen atom to which they are attached represent a 5- or 6-membered ring optionally containing an additional heteroatom selected from N or O, in which ring any nitrogen atom present may optionally be substituted with a $C_{1-4}$ alkyl group; or $M^6$ represents a 5- or 6-membered heterocyclic ring system containing 1 or 2 heteroatoms selected from N or O.

6. A compound as claimed in claim 1 wherein $M^2$-$M^3$-$M^4$ represents an α-amino carboxylic acid or a methyl ester or amide thereof; or $M^2$-$M^3$-$M^4$ represents a β- or γ-amino sulphinic or sulphonic acid or a methyl ester thereof.

7. A compound as claimed in claim 1 wherein $M^2$-$M^3$-$M^4$ represents a methylsulphonylethylamino, methylsulphinylethylamino, methylsulphonylpropylamino, methylsulphinylpropylamino, methylsulphonamidoethylamino, sarcosinamide, glycine, glycinamide, or glycine methyl ester group.

8. A compound as claimed in claim 1 wherein $M^1$-$M^5$ represents a piperazinyl-methyl, methylpiperazinyl-methyl, piperidinyl-methyl, prolinamidomethyl, N,N-dimethylprolinamido-methyl, isopropylacetamido or N-morpholinoacetamido group.

9. A compound as claimed in claim 1 wherein $M^2$-$M^3$-$M^6$ represents a pyridylamino group.

10. A compound as claimed in claim 1 wherein $R^1$ is selected from the group consisting phenyl, furan, imidazole, tetrazole, triazole, pyrrolidine, piperazine, piperidine and oxadiazole.

11. A compound as claimed in claim 10 wherein $R^1$ is selected from furan, imidazole and oxadiazole.

12. The compound of claim 11, wherein $R^1$ is furan.

13. A compound as claimed in claim 1 wherein $R^3$ is benzyl, halo-, dihalo- and trihalobenzyl, α-methylbenzyl, phenyl, halo-, dihalo- and trihalophenyl, pyridyl, pyridylmethyl, pyridyloxy, pyridylmethoxy, thienylmethoxy, dioxolanylmethoxy, cyclohexylmethoxy, phenoxy, halo-, dihalo- and trihalophenoxy, phenylthio, benzyloxy, halo-, dihalo- and trihalobenzyloxy, $C_{1-4}$ alkoxybenzyloxy, phenyloxalyl or benzenesulphonyl.

14. A compound as claimed in claim 13 wherein $R^3$ is benzyl, fluorobenzyl, benzyloxy, fluorobenzyloxy, pyridylmethyl, phenyl, benzenesulphonyl, phenoxy or fluorophenoxy.

15. A compound as claimed in claim 1 wherein X represents N; U represents a pyridine ring; and the group $R^1$ is in the 6-position of the pyridopyrimidine ring system.

16. A compound of formula (I) or a salt or solvate thereof as claimed in claim 1, wherein X represents N; U represents a pyridine ring; Y represents $NR^a$, wherein $R^a$ is hydrogen or $C_{1-4}$ alkyl; $R^1$ represents furan, thiophene, pyrrole, pyridine, pyrimidine, pyrazine, oxazole, isoxazole, oxadiazole, imidazole, tetrazole, triazole, dioxolane or a partially or fully hydrogenated derivative of any of these groups, substituted by one or more groups selected from hydroxy-$C_{1-4}$ alkyl, hydroxy-$C_{1-4}$ alkanoyl($C_{1-4}$ alkyl)-amino, 1,3-dioxolan-2-yl, $C_{1-4}$ alkylamino-$C_{1-4}$ alkyl or di($C_{1-4}$alkyl)-amino-$C_{1-4}$ alkyl, and optionally further substituted by one or more $C_{1-4}$ alkyl groups; $R^2$ represents hydrogen; $R^1$ represents hydrogen or methyl; n is 1; and $R^3$ represents phenyl, benzyl, o-methylbenzyl, fluorobenzyl, benzenesulphonyl, phenoxy, fluorophenoxy, benzyloxy or fluorobenzyloxy.

17. The compound of claim 16 or a salt or solvate thereof, wherein $R^1$ is furan, oxadiazole or imidazole, substituted by one or more groups selected from hydroxy-$C_{1-4}$ alkyl, hydroxy-$C_{1-4}$ alkanoyl($C_{1-4}$ alkyl)-amino, 1,3-dioxolan-2-yl, $C_{1-4}$alkylamino-$C_{1-4}$alkyl or di(Ci-alkyl)-amino-$C_{1-4}$alkyl, and optionally further substituted by one or more $C_{1-4}$alkyl groups.

18. A compound of formula (I) or a salt or solvate thereof as claimed in claim 1, wherein X represents N; U represents a pyridine ring; Y represents NR$^a$, wherein R$^a$ is hydrogen or C$_{1-4}$ alkyl; R$^1$ represents furan, thiophene, pyrrole, pyridine, pyrimidine, pyrazine, oxazole, isoxazole, oxadiazole, imidazole, tetrazole, triazole, dioxolane or a partially or fully hydrogenated derivative of any of these groups, substituted by one or more groups selected from methyl sulphonylethylaminomethyl, methylsulphonylethylamino-carbonyl, methylsulphinyl ethylamino-methyl, methylsulphinylethylamino-carbonyl, methylsulphonylpropylamino-methyl, methylsulphinyl propylamino-methyl, methylsulphonyl propyamino-carbonyl, methylsulphinylpropylamino-carbonyl, methylsulphonylethyl-(methylamino)-methyl, methylsulphonylethyl-(methylamino)carbonyl, methylsulphinylethyl-(methylamino)-methyl, methylsulphinylethyl(methylamino)-carbonyl, methylsulphonylpropyl-(methylamino)-methyl, methylsulphinylpropyl-(methylamino)-methyl, methylsulphonylpropyl(methylamino)carbonyl, methylsulphinylpropyl-(methylamino)-carbonyl, methylsulphonamidoethylamino-methyl, methylsulphonamidopropylamino-methyl, sarcosinamidomethyl, glycinylmethyl, glycinamidomethyl, glycinylmethyl methyl ester, acetylaminoethylaminomethyl, piperazinylmethyl, methylpiperazinyl methyl, piperidinylmethyl, N-(prolinamido)methyl, (N,N-dimethylprolinamido)methyl, pyrdylaminomethyl, cyclopropylaminomethyl, N-(piperidin-4-yl)-N-methylaminomethyl, N,N-dimethylaminoprop-2-ylaminomethyl, N-(2dimethylaminoethyl)-N-ethylaminomethyl, isopropylacetamido, N-morpholinylacetamido or tetrahydrofurano methylaminomethyl, and optionally further substituted by one or more C$_{1-4}$alkyl groups; R$^2$ represents hydrogen; R$^5$ represents hydrogen or methyl; n is 1; and R$^3$ represents phenyl, benzyl, α-methylbenzyl, fluorobenzyl, benzenesulphonyl, phenoxy, fluorophenoxy, benzyloxy or fluorobenzyloxy.

19. The compound of claim 18 or a salt or solvate thereof, wherein R$^1$ is furan, oxadiazole or imidazole, substituted by one or more groups selected from methyl sulphonylethylaminomethyl, methylsulphonylethylamino-carbonyl, methylsulphinyl ethylamino-methyl, methylsulphinylethylamino-carbonyl, methylsulphonylpropylaminomethyl, methylsulphinylpropylamino-methyl, methylsulphonylpropyamino-carbonyl, methylsulphinylpropylamino-carbonyl, methylsulphonylethyl-(methylamino)-methyl, methylsulphonylethyl-(methylamino)-carbonyl, methylsulphinylethyl-(methylamino)methyl, methylsulphinylethyl-(methylamino)-carbonyl, methylsulphonylpropyl(methylamino)-methyl, methylsulphinylpropyl-(methylamino)-methyl, methyl sulphonylpropyl-(methylamino)-carbonyl, methylsulphinylpropyl-(methylamino)-carbonyl, methylsulphonamidoethylamino-methyl, methylsulphonamidopropylamino-methyl, sarcosinamidomethyl, glycinylmethyl, glycinamidomethyl, glycinylmethyl methyl ester, acetylaminoethylaminomethyl, piperazinylmethyl, methylpiperazinylmethyl, piperidinyl methyl, N-(prolinamido)methyl, (N,N-dimethylprolinamido)methyl, pyrdylaminomethyl, cyclopropylaminomethyl, N-(piperidin-4-yl)-N-methylaminomethyl, N,N-dimethyl aminoprop-2-ylaminomethyl, N-(2-dimethylaminoethyl)-N-ethylaminomethyl, isopropylacetamido, N-morpholinylacetamido or tetrahydrofuranomethylaminomethyl, and optionally further substituted by one or more C$_{1-4}$alkyl groups.

20. A compound of formula (I) or a salt or solvate thereof as claimed in claim 16 wherein X represents N; U represents a pyridine ring; Y represents NR$^a$, wherein R$^a$ is hydrogen or C$_{1-4}$ alkyl; R$^1$ represents furan, oxadiazole or imidazole, substituted by a group selected from hydroxy-C$_{1-4}$ alkyl, 1,3-dioxolan-2-yl, C$_{1-4}$ alkylamino-C$_{1-4}$ alkyl or di(C$_{1-4}$alkyl)-amino-C$_{1-4}$alkyl, methylsulphonylethylaminomethyl, methylsulphinylethylamino-methyl, methylsulphonylpropylaminomethyl, methylsulphonylethyl-(methylamino)-methyl, methylsulphonamidoethylamino-methyl, sarcosinamidomethyl, glycinylmethyl, glycinylmethyl methyl ester, acetylaminoethyl aminomethyl, piperazinylmethyl, methylpiperazinylmethyl, piperidinylmethyl, N-(prolinamido)methyl, (N,N-dimethylprolinamido)methyl and pyrdylaminomethyl; R$^2$ represents hydrogen; R$^5$ represents hydrogen or methyl; n is 1; and R$^3$ represents fluorobenzyloxy, benzenesulphonyl or benzyloxy.

21. The compound of claim 20 or a salt or a solvate thereof, wherein R$^1$ is furan, substituted by a group selected from hydroxy-C$_{1-4}$ alkyl, 1,3-dioxolan-2-yl, C$_{1-4}$alkylamino—C$_{1-4}$alkyl or di(C$_{1-4}$alkyl)-amino-C$_{1-4}$alkyl, methylsulphonylethyl- aminomethyl, methylsulphinylethylamino-methyl, methylsulphonylpropylamino-methyl, methyl sulphonylethyl-(methylamino)-methyl, methylsulphonamidoethylamino-methyl, sarcosinamidomethyl, glycinylmethyl, glycinyl methyl methyl ester, acetylaminoethyl aminomethyl, piperazinylmethyl, methylpiperazinylmethyl, piperidinylmethyl, N-(prolinamido)methyl, (N,N-dimethylprolinamido)methyl and pyridylaminomethyll and R$^3$ is benzyloxy.

22. A compound as claimed in claim 1 selected from:
(4-Benzyloxy-phenyl)-(6-(5-piperidin-1-ylmethyl)-furan-2-yl)-pyrido[3,4-d]pyrimidin-4-yl)-amine;
(4-Benzyloxy-phenyl)-(6-(5-(4-methyl-piperazin-1-ylmethyl)-furan-2-yl)pyrido[3,4-d]pyrimidin-4-yl)-amine;
(4-Benzyloxy-phenyl)-(6-(5-((2-methanesulphonyl-ethylamino)methyl)-furan-2-yl)pyrido[3,4-d]pyrimidin-4-yl)-amine;
((5-(4-(4-Benzyloxy-phenylamino)-pyrido[3,4-d]pyrimidin-6-yl)-furan-2-ylmethyl)-amino)-acetic acid methyl ester;
(4-Benzyloxy-phenyl)-(6-(5-(pyridin-3-ylaminomethyl)-furan-2-yl)-pyrido[3,4-d]pyrimidin-4-yl)-amine;
(4-Benzyloxy-phenyl)-6-(5-(dimethylaminomethyl)-furan-2-yl)-pyrido[3,4-d]pyrimidin-4-yl)-amine;
(2S)-1-(5-(4-(4-Benzyloxy-phenylamino)-pyrido[3,4-d]pyrimidine-6-yl)-furan-2-ylmethyl)-pyrrolidine-2-carboxylic acid amide;
2-((5-(4-(4-Benzyloxy-phenylamino)-pyrido[3,4-d]pyrimidin-6-yl)-furan-2-ylmethyl)methylamino)-acetamide;
(4-Benzyloxy-phenyl)-(6-(5-((2-methanesulphinyl-ethylamino)-methyl)-furan-2-yl)pyrido[3,4-d]pyrimidin-4-yl)-amine;
((5-(4-(4Benzyloxy-phenylamino)-pyrido[3,4-d]pyrimidine-6-yl)-furan-2-ylmethyl)-amino)-acetic acid;

(5-(4-(4-Benzyloxy-phenylamino)-pyrido[3,4-d]
pyrimidin-6-yl)-furan-2-yl)-methanol;

(2R)-1-{5-8 4-(4- Benzyloxy-phenylamino)-
pyridopyrimidin-6-yl]-furan-2-ylmethyl}-pyrrolidine-
2-carboxylic acid amide;

(4-Benzyloxy-phenyl)-(6-(5-((3-methanesulphonyl-
propylamino)methyl)-furan-2-yl)pyrido[3,4-d]
pyrimidin-4-yl)-amine;

(4-Benzyloxy-phenyl)-(6-(5-(((2-methanesulphonyl-
ethyl)-methyl-amino)-methyl)-furan2-yl)-pyrido[3,4-
d]pyrimidin-4-yl)-amine;

(2S)-1-{-5-[4-(4-Benzyloxy-phenylamino)-pyrido[3,4-d]
pyrimidin-6-yl]-furan-2-ylmethyl}-pyrrolidine-2-
carboxylic acid dimethylamide;

N-(2-((5-(4-(4-Benzyloxy-phenylamino)-pyrido[3,4-d]
pyrimidin-6-yl)-furan-2-ylmethyl)-amino)-ethyl)-
methanesulphonamide;

(4-Benzyloxyphenyl)-(6-(5-(1,3-dioxolan-2-yl-furan-2-
yl)-pyrido[3,4-d]pyrimidin-4-yl)-amine;

and salts or solvates thereof.

23. A compound as claimed in claim 22 selected from:

4-Benzyloxy-phenyl)-(6-(5-((2-methanesulphonyl-
ethylamino)methyl)-furan-2-yl)1-pyrido[3,4-d]
pyrimidin-4-yl)-amine;

(2)-1-1-5-(4-(4-Benzyloxy-phenylamino)-pyrido[3,4-d]
pyrimidine-6-yl)-furan-2-ylmethyl)-pyrrolidine-2-
carboxylic acid amide;

(2R)-1-{-5-[4-(4-Benzyloxy-phenylamino)-pyrido[3,4-d]
pyrimidin-6-yl]-furan-2-ylmethyl}-pyrrolidine-2-
carboxylic acid amide;

(2S)-1-{-5-[4-(4-Benzyloxy-phenylamino)-pyrido[3,4-d]
pyrimidin-6yl]-furan-2-ylmethyl}pyrrolidine-2-
carboxylic acid dimethylamide;

and salts or solvates thereof.

24. A process for the preparation of a compound of formula (I) as defined in claim 1 which comprises the steps:

(a) the reaction of a compound of formula (II)

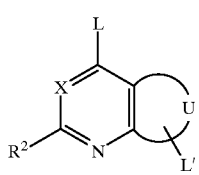
(II)

wherein U, X and $R^2$ are as defined in claim 1 and L and L' are leaving groups, with a compound of formula (III)

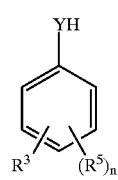
(III)

wherein Y, $R^3$, $R^5$ and n are as defined in claim 1 to prepare a compound of formula (IV)

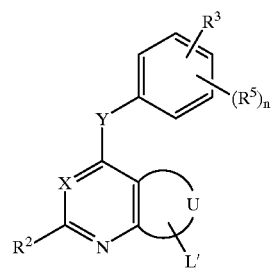
(IV)

and subsequently (b) reaction with an appropriate reagent to substitute the group $R^1$ onto the ring U by replacement of the leaving group L';

and, if desired, (c) subsequently converting the compound of formula (I) thereby obtained into another compound of formula (I) by means of appropriate reagents.

25. A pharmaceutical formulation comprising at least one compound as claimed in claim 1 together with one or more pharmaceutically acceptable carriers, diluents or excipients.

26. A pharmaceutical formulation as claimed in claim 25 in unit dosage form and containing a compound in an amount of from 70 to 700 mg.

27. A method of treatment of a human or animal subject suffering from a disorder mediated by aberrant protein tyrosine kinase activity including cancer, malignant tumors and psoriasis which comprises administering to the human or animal subject an effective amount of a compound as claimed in claim 1.

28. A method of treating a disorder mediated by aberrant protein tyrosine kinase activity in a human or animal subject, wherein at least one kinase selected from the group consisting of c-erb-B2, EGFr, and c-erb-B4 exhibits aberrant activity, comprising administering to the human or animal an effective amount of a compound of formula I:

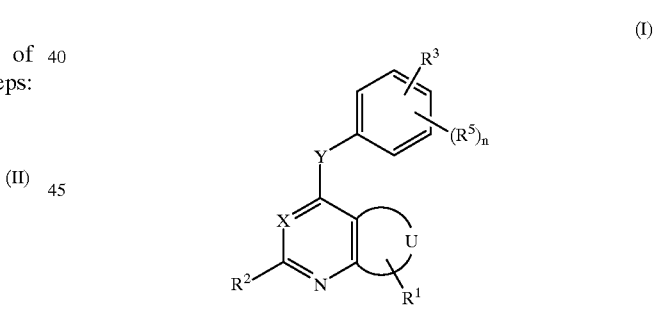
(I)

or a salt or solvate thereof;
wherein X is N;
Y is a group W(CH$_2$), (CH$_2$)W, or W, in which W is 0, S(O)$_m$ wherein m is 0, 1 or 2, or NR$^a$ wherein R$^a$ is hydrogen or a $C_{1-8}$ alkyl group;
$R^1$ is selected from the group consisting of phenyl, furan, thiophene, pyridine, pyrimidine, pyrazine, pyrrole, oxazole, isooxazole, oxadiazole, thiazole, isothiazole, triazole, tetrazole and imidazole ring or a hydrogenated derivative of the aforementioned, the ring being substituted:
either (a) by one or more groups selected from dioxolanyl, hydroxy-$C_{1-4}$ alkyl, $C_{1-4}$ alkylamino-$C_{1-4}$ alkyl, or di-amino-$C_{1-4}$ alkyl;
or (b) by one or more groups independently selected from $M^1$-$M^2$-$M^3$-$M^4$, $M^1$-$M^2$-$M^{3'}$-$M^6$ wherein M¹ represents a $C_{1-4}$ alkyl group, wherein optionally a $CH_2$ group is replaced by a CO group;

M² represents $NR^{12}$ or $CR^{12}R^{13}$, in which $R^{12}$ and $R^{13}$ each independently represent H or $C_{1-4}$ alkyl;

M³ represents a $C_{1-4}$ alkyl group;

M³ represents a $C_{1-4}$ alkyl group or is absent;

M⁴ represents CN, $NR^{12}S(O)_mR^{13}$, $S(O)_mNR^{14}R^{15}$, $CONR^{14}R^{15}$, $S(O)_mR^{13}$ or $CO_2R^{13}$, in which $R^{12}$, $R^{13}$ and m are as hereinbefore defined and $R^{14}$ and $R^{15}$ each independently represent H or $C_{1-4}$ alkyl, or $R^{14}$ and $R^{15}$ together with the nitrogen atom to which they are attached represent a 5-or 6-membered ring optionally containing 1 or 2 additional heteroatoms selected from N, O or $S(O)_m$ in which ring any nitrogen atom present may optionally be substituted with a $C_{1-4}$ alkyl group;

M⁵ represents the group $NR^{14}R^{15}$ or the group

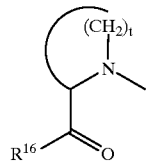

in which t represents 2 to 4 and $R^{16}$ represents OH, $OC_{1-4}$ alkyl or $NR^{14}R^{15}$; and M⁶ represents a $C_{3-6}$ cycloalkyl group, the group $NR^{14}R^{15}$ or a 5- or 6-membered heterocyclic ring system containing 1 to 4 heteroatoms selected from N, O or S;

and R¹ is optionally further substituted by one or two halogeno, $C_{1-4}$ alkyl or $C_{1-4}$ alkoxy groups;

R² represents hydrogen;

each R⁵ is independently selected from the group consisting of hydrogen, hydroxy, halogen, $C_{1-4}$ alky, $C_{1-4}$ alkoxy, $C_{1-4}$ alkylamino, di-amino, $C_{1-4}$ alkylthio, $C_{1-4}$ alkylsulphinyl, $C_{1-4}$ alkylsulphonyl, $C_{1-4}$ alkylcarbonyl, $C_{1-4}$ alkylcarbamoyl, di-carbamoyl, carbamyl, $C_{1-4}$ alkoxycarbonyl, cyano, nitro and trifluoromethyl, and n is 1, 2 or 3;

R³ is a group $ZR^4$ wherein Z is joined to $R^4$ through a $(CH_2)p$ group in which p is 0, 1 or 2 and Z is oxygen, dicarbonyl, $OCH_2$, CH(CN), $S(O)_m$, or $NR^b$ where $R^b$ is hydrogen or $C_{1-4}$ alkyl; and R⁴ is an optionally substituted phenyl, dioxianyl, thienyl, cyclohexyl, or pyridyl group;

wherein any optional substituent on R⁴ is either (a) selected from the group consisting of $(CH_2)_qS(O)_m$—$C_{1-4}$ alkyl, $(CH_2)_qS(O)_m$—$C_{3-6}$ cycloalkyl, $(CH_2)_q SO_2NR^8R^9$, $(CH_2)_qNR^6R^9$, $(CH_2)_qCO_2R^8$, $(CH_2)_q OR^8$, $(CH_2)_qCONR^8R^9$, $(CH_2)_qNR^8COR^9$, $(CH_2)_q COR^8$, $(CH_2)_qR^8$, $NR^8SO_2R^9$ and $S(O)_mR^8$, wherein q is an integer from 0 to 4 inclusive and m is as defined above; and wherein $R^8$ and $R^9$ are independently selected from the group consisting of hydrogen, $C_{1-4}$ alkyl, $C_{3-6}$ cycloalkyl, aryl, a 5- or 6- membered saturated or unsaturated heterocyclic ring which may be the same or different and which contains one or more heteroatoms which are selected from N, O or $S(O)_m$ with the proviso that the heterocyclic ring does not contain two adjacent O or $S(O)_m$ atoms; or (b) is selected from the group consisting of halogen, trifluoromethyl, triflourmethoxy, nitro, and cyano; and represents

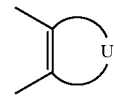

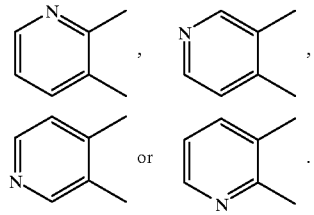

29. A method of treating a disorder mediated by aberrant protein tyrosine kinase activity in a human or animal subject, wherein at least two kinases selected from the group consisting of c-erb-B2, EGFr, and c-erb-B4 exhibits aberrant activity, comprising administering to the human or animal an effective amount of a compound of formula I:

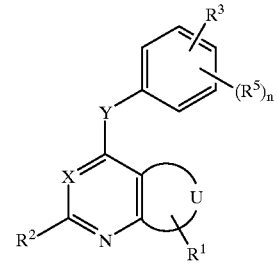

(I)

or a salt or solvate thereof;

wherein X is N;

Y is a group $W(CH_2)$, $(CH_2)W$, or W, in which W is O, $S(O)_m$ wherein m is 0, 1 or 2, or $NR^a$ wherein $R^a$ is hydrogen or a $C_{1-8}$ alkyl group;

R¹ is selected from the group consisting of phenyl, furan, thiophene, pyridine, pyrimidine, pyrazine, pyrrole, oxazole, isooxazole, oxadiazole, thiazole, isothiazole, triazole, tetrazole and imidazole ring or a hydrogenated derivative of the aforementioned, the ring being substituted:

either (a) by one or more groups selected from dioxolanyl, $C_{1-4}$ alkyl, $C_{1-4}$ alkylamino-$C_{1-4}$ alkyl, or di-amino-$C_{1-4}$ alkyl;

or (b) by one or more groups independently selected from $M^1$-$M^2$-$M^3$-$M^4$, $M^1$-$M^5$ or $M^1M^2$-$M^3$-$M^6$ wherein M¹ represents a $C_{1-4}$ alkyl group, wherein optionally a $CH_2$ group is replaced by a CO group;

M² represents $NR^{12}$ or $CR^{12}R^{13}$, in which $R^{12}$ and $R^{13}$ each independently represent H or $C_{1-4}$ alkyl;

M³ represents a $C_{1-4}$ alkyl group;

M³' represents a $C_{1-4}$ alkyl group or is absent;

M⁴ represents CN, $NR^{12}S(O)_mR^{13}$, $S(O)_mNR^{14}R_{15}$, $S(O)_mR^{13}$, in which $R^{12}$, $R^{13}$ and m are as hereinbefore defined and $R^{14}$ and $R^{15}$ each independently represent H or $C_{1-4}$ alkyl, or $R^{14}$ and $R^{15}$ together with the nitrogen atom to which they are attached represent a 5-or 6-membered ring optionally containing 1 or 2 additional heteroatoms selected from N, O or $S(O)_m$ in which ring any nitrogen atom present may optionally be substituted with a $C_{1-4}$ alkyl group;

$M^5$ represents the group $NR^{14}R^{15}$ or the group

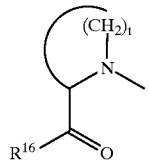

in which t represents 2 to 4 and $R^{16}$ represents OH, $OC_{1-4}$ alkyl or $NR^{14}R^{15}$; and $M^6$ represents a $C_{3-6}$ cycloalkyl group, the group $NR^{14}R^{15}$, or a 5- or 6-membered heterocyclic ring system containing 1 to 4 heteroatoms selected from N, O or S;

and $R^1$ is optionally further substituted by one or two halogeno, $C_{1-4}$ alkyl or $C_{1-4}$ alkoxy groups;

$R^2$ represents hydrogen;

each $R^5$ is independently selected from the group consisting of hydrogen, hydroxy, halogen, $C_{1-4}$ alkyl, $C_{1-4}$ alkoxy, $C_{1-4}$ alkylamino, di-amino, $C_{1-4}$ alkylthio, $C_{1-4}$ alkylsulphinyl, $C_{1-4}$ alkylsulphonyl, $C_{1-4}$ alkylcarbonyl, $C_{1-4}$ alkylcarbamoyl, di-carbamoyl, carbamyl, $C_{1-4}$ alkoxycarbonyl, cyano, nitro and trifluoromethyl, and n is 1, 2 or 3;

$R^3$ is a group $ZR^4$ wherein Z is joined to $R^4$ through a $(CH_2)p$ group in which p is 0, 1 or 2 and Z is oxygen, dicarbonyl, $OCH_2$, CH(CN), $S(O)_m$, or $NR^b$ where $R^b$ is hydrogen or $C_{1-4}$ alkyl; and $R^4$ is an optionally substituted phenyl, dioxlanyl, thienyl, cyclohexyl, or pyridyl group;

wherein any optional substituent on $R^4$ is either (a) selected from the group consisting of $(CH_2)_qS(O)_m$— $C_{1-4}$alkyl, $(CH_2)_qS(O)_m$—$C_{3-6}$ cycloalkyl, $(CH_2)_q SO_2NR^8R^9$, $(CH_2)NR^8R^9$, $(CH_2)_qCO_2R^8$, $(CH_2)_q OR^8$, $(CH_2)_qCONR^8R^9$, $(CH_2)_qNR^8COR^9$, $(CH_2)_q COR^8$, $(CH_2)_qR^8$, $NR^8SO_2R^9$ and $S(O)_mR^8$, wherein q is an integer from 0 to 4 inclusive and m is as defined above; and wherein $R^8$ and $R^9$ are independently selected from the group consisting of hydrogen, $C_{1-4}$ alkyl, $C_{3-6}$ cycloalkyl, aryl, a 5- or 6- membered saturated or unsaturated heterocyclic ring which may be the same or different and which contains one or more heteroatoms which are selected from N, O or $S(O)_m$ with the proviso that the heterocyclic ring does not contain two adjacent O or $S(O)_m$ atoms; or (b) is selected from the group consisting of halogen, trifluoromethyl, trifluormethoxy, nitro, and cyano; and

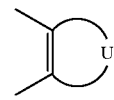

represents

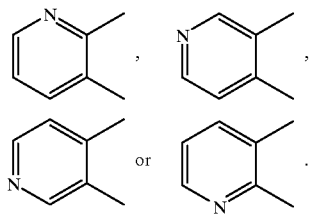

* * * * *